(12) United States Patent
Blattner et al.

(10) Patent No.: US 11,970,725 B2
(45) Date of Patent: Apr. 30, 2024

(54) **REDUCED GENOME *E. COLI* LACKING TOXIN-ANTITOXIN GENES**

(71) Applicant: SCARAB GENOMICS LLC, Madison, WI (US)

(72) Inventors: Frederick R. Blattner, Madison, WI (US); Robert E. Novy, Verona, WI (US); David A. Frisch, Fitchburg, WI (US); Charles Landry, Fitchburg, WI (US); Hyunsic Choi, Madison, WI (US); Eric A. Steffen, Mount Horeb, WI (US); John Brandon, Madison, WI (US)

(73) Assignee: Scarab Genomics LLC, Madison, WI (US)

( * ) Notice: Subject to any disclaimer, the term of this patent is extended or adjusted under 35 U.S.C. 154(b) by 0 days.

(21) Appl. No.: 18/299,479

(22) Filed: Apr. 12, 2023

(65) Prior Publication Data

US 2023/0287472 A1 Sep. 14, 2023

Related U.S. Application Data

(62) Division of application No. 16/644,444, filed as application No. PCT/US2018/049422 on Sep. 4, 2018, now Pat. No. 11,667,944.

(60) Provisional application No. 62/554,443, filed on Sep. 5, 2017.

(51) Int. Cl.
| | | |
|---|---|---|
| *C12N 1/21* | (2006.01) | |
| *C07K 14/21* | (2006.01) | |
| *C07K 14/285* | (2006.01) | |
| *C07K 14/34* | (2006.01) | |
| *C12N 1/20* | (2006.01) | |
| *C12N 9/18* | (2006.01) | |
| *C12P 21/06* | (2006.01) | |

(52) U.S. Cl.
CPC .............. *C12P 21/06* (2013.01); *C07K 14/21* (2013.01); *C07K 14/285* (2013.01); *C07K 14/34* (2013.01); *C12N 1/20* (2013.01); *C12N 9/18* (2013.01); *C07K 2319/02* (2013.01)

(58) Field of Classification Search
None
See application file for complete search history.

(56) References Cited

U.S. PATENT DOCUMENTS

| | | | | |
|---|---|---|---|---|
| 11,667,944 B2 * | 6/2023 | Blattner | ................ | C07K 14/245 435/69.7 |
| 2011/0111458 A1 * | 5/2011 | Masuda | .................. | C12P 13/04 435/252.33 |

FOREIGN PATENT DOCUMENTS

| | | | | |
|---|---|---|---|---|
| WO | WO-2015134402 A1 * | 9/2015 | ............... | C07K 1/18 |

* cited by examiner

*Primary Examiner* — David Steadman
(74) *Attorney, Agent, or Firm* — Much Shelist, PC; Christopher M. Cabral

(57) ABSTRACT

Provided herein are *E. coli* host strains with improved capacity for producing recombinant proteins.

13 Claims, 30 Drawing Sheets

Specification includes a Sequence Listing.

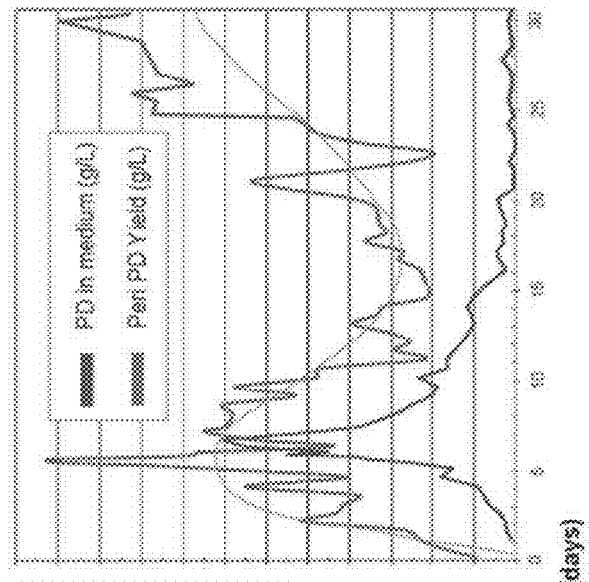
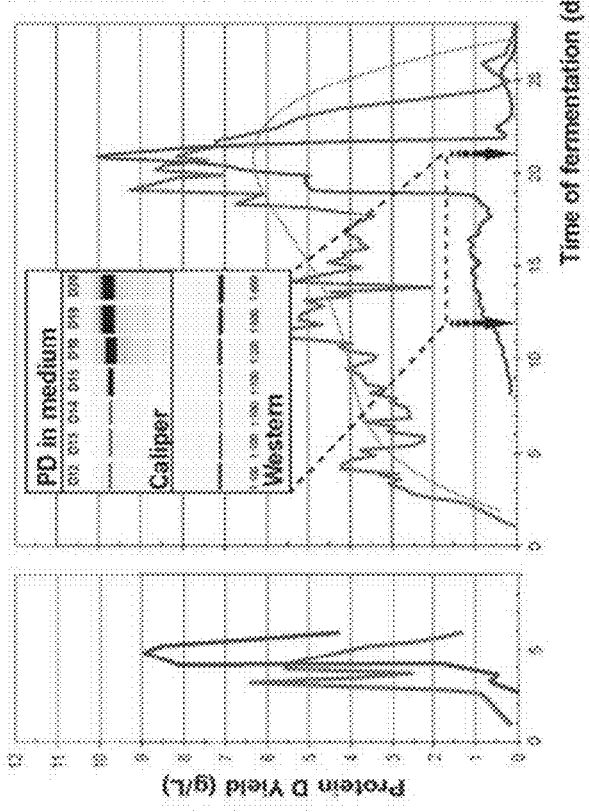

| | SG9369<br>T89 Meta ToxATox LoxMut recA<br>DOX-yfiQ-CRM197 | | | | SG9395<br>T89 Meta ToxATox LoxMut recA<br>DOX-yfiQ-CRM197-RBS-C.A. pldA | | | | SG9397<br>T89 Meta ToxATox LoxMut recA<br>DOX-yfiQ-CRM197-RBS1-C.A. pldA | | | |
|---|---|---|---|---|---|---|---|---|---|---|---|---|
| | Tris/EDTA | | | | | | | | | | | |
| OD at induct | 2.73 | | | | 2.74 | | | | 2.93 | | | |
| OD at Harvest | 2.2 | 2.25 | 2.35 | 2.35 | 2.44 | 2.74 | 3.46 | 3.57 | 2.33 | 3.46 | 3.37 | 3.35 |
| DOX | 0 | 100 | 250 | 400 | 0 | 100 | 250 | 400 | 0 | 100 | 250 | 400 |
| CRM197 g/L | 0 | 0.7 +/- 0.2 | 0.4 +/- 0.1 | 0.2 +/- 0.2 | 0.1 | 2.8 +/- 0.4 | 3.1 +/- 0 | 3.4 +/- 0.6 | 0 | 2.5 +/- 0 | 2.8 +/- 0.2 | 2.9 +/- 0.3 |
| Purity % | | | | | | 25 | 23 | 22 | | 32 | 30 | 27 |

| New Caliper Chip used | SG9461-62<br>T69 Meta recA<br>pSG9353 | | | | SG9457<br>T69 Meta T/AT recA<br>pSG9353 | | | | SG9369<br>T69 Meta T/AT LowMut recA<br>pSG9353 | | | |
|---|---|---|---|---|---|---|---|---|---|---|---|---|
| | PERIPLASM | | | | | | | | | | | |
| OD at Induct | 2.70 | | 2.66 | | 2.66 | | | | 2.96 | | | |
| OD at Harvest | 2.35 | 2.30 | 2.36 | 2.33 | 1.38 | 2.34 | 2.39 | 2.34 | 2.38 | 2.28 | 2.55 | 2.58 |
| DOX nM | 50 | 100 | 50 | 100 | 50 | 100 | 50 | 100 | 50 | 100 | 50 | 100 |
| CRM197 g/L* | 3.9 | 3.8 | 3.8 | 4.0 | 4.8 | 5.7 | 4.7 | 5.1 | 5.0 | 4.9 | 5.1 | 5.4 |
| Purity % | 63 | 65 | 65 | 62 | 54 | 70 | 70 | 71 | 73 | 68 | 65 | 67 |
| | 3.9 +/- 0.1 | | | | 5.1 +/- 0.5 | | | | 5.1 +/- 0.2 | | | |

REDUCED GENOME E. COLI LACKING TOXIN-ANTITOXIN GENES

CROSS-REFERENCE TO RELATED APPLICATIONS

This application is a divisional of U.S. patent application Ser. No. 16/644,444, filed Mar. 4, 2020, which is the 35 U.S.C. 371 National Stage of International Application Number PCT/US2018/049422, filed Sep. 4, 2018, which claims the benefit of U.S. Provisional Patent Application Ser. No. 62/554,443, filed Sep. 5, 2017, the full disclosures of which are incorporated herein by reference.

SEQUENCE LISTING SUBMISSION VIA EFS-WEB

A computer readable XML file, entitled "010447-5043-US-01-Sequence-Listing", created on Apr. 11, 2023, with a file size of 11,965 bytes contains the sequence listing for this application and is hereby incorporated by reference in its entirety.

FIELD OF THE INVENTION

Methods and compositions for enhancing expression and recovery of difficult to produce proteins such as single-chain antibodies, single-chain fragments, and those suitable as carriers for polysaccharides and haptens are provided.

BACKGROUND OF THE INVENTION

Thirty percent of FDA approved recombinant therapeutic proteins are made in *E. coli* and include important vaccine components such as carrier proteins, single-chain antibodies, and single-chain antibody fragments. However, the standard method of producing recombinant proteins from *E. coli* has not changed in decades. Traditional fed-batch fermenters are used to culture target-containing bacteria in increasingly large batches that are then subjected to mass homogenization prior to the often complex and arduous task of protein purification. The process is expensive, time consuming and often requires difficult and extensive purification procedures resulting in loss of yield.

Cross-reactive material 197 (CRM197), a mutant non-toxic form of diphtheria toxin, is an approved carrier protein used in a variety of successful conjugate vaccines. However, demand for CRM197 exceeds supply due to problems with its manufacture. The original host, *Corynebacterium diphtheriae*, generates low levels of CRM197 (0.1 to 0.2 g/L) and requires biosafety level 2 facilities. Potential reversion of CRM197 to wild type toxin remains a problem in alternative hosts such as *Pseudomonas fluorescens* and most *E. coli* strains and residual CRM197 toxicity causes significant physiological stress in these hosts, limiting production. Further, in most *E. coli* hosts, CRM197 accumulates in an insoluble form (which aggregates into inclusion bodies) further reducing yield and complicating downstream purification steps. Many *E. coli* strains favored for fermentation are subject to activation of cryptic prophage, insertion elements and other mutation-generating, stress-induced systems that can 1) affect the expression vector or 2) destroy the host, in both cases leading to rapid and total loss of production in batch mode and precluding the use of these *E. coli* hosts in extended continuous fermentation processes.

Due to the importance of difficult-to-produce carrier proteins such as CRM197, non-acylated Protein D of *Haemophilus influenzae* (PD) and carrier protein exoprotein A (EPA) of *Pseudomonas aeruginosa*, as well as single-chain antibody, single-chain antibody fragment scFab YMF10, single-chain antibody variable fragment scFv 75127, there is a need for improved and cost-effective methods to produce and purify such proteins from *E. coli* host cells.

SUMMARY OF THE INVENTION

In several embodiments, methods for achieving release of periplasmic-targeted recombinant proteins in *E. coli* are provided comprising co-expressing an endogenous *E. coli* phospholipase with the recombinant protein. In some related embodiments, the *E. coli* host strain is contacted with an extraction buffer following induction of the recombinant protein and phospholipase.

In several embodiments, a method for producing a recombinant protein of interest is provided comprising fermentation of a recombinant (e.g. reduced genome) *E. coli* strain carrying a heterologous nucleic acid comprising a nucleotide sequence encoding the recombinant protein of interest fused to a signal sequence that directs transfer of the protein of interest to the periplasm, said nucleotide sequence operably linked to an expression control sequence, wherein the *E. coli* strain co-expresses one or more *E. coli* phospholipases with the recombinant protein of interest. Exemplary periplasmic targeting signals include those described in paragraphs [0055]-[0059] of United States Patent Application Publication No. 20170073379, the entire disclosure of which is incorporated herein by reference. Representative signal sequences capable of directing CRM197 to the periplasm are listed at the end of paragraph [0057] of US 20170073379 and preferably are selected from an OmpA, MalE, HdeA, OppA, HdeB, GlnH, MglB, agp, OmpC, RbsB, FkpA or YtfQ signal sequence, more preferably from an OmpA, OmpF or YtfQ signal sequence. In some preferred embodiments, a YtfQ signal sequence directs PD, EPA or CRM197 to the periplasm. In some preferred embodiments, an OmpA signal sequence directs single-chain antibody fragment scFab YMF10, single-chain antibody variable fragment scFv 75127 to the periplasm.

Any *E. coli* phospholipase may be co-expressed with a protein of interest in an *E. coli* host according to the methods herein described. In one embodiment, the *E. coli* strain comprises a nucleic acid segment comprising a nucleotide sequence encoding glycerophosphoryl diester phosphodiesterase (glpQ; b2239; GenBank Ref. No. NP_416742.1; SEQ ID NO: 1). In another embodiment, the *E. coli* strain comprises a nucleic acid segment comprising a nucleotide sequence encoding Aes (ybaC; b0476; GenBank Ref. No. NP_415009.1; SEQ ID NO: 2). In another embodiment, the *E. coli* strain comprises a nucleic acid segment comprising a nucleotide sequence encoding Lysophospholipase L2 (pldB; b3825; GenBank Ref. No. YP_026266.1; SEQ ID NO: 3). In a preferred embodiment, the *E. coli* strain comprises a nucleic acid segment comprising a nucleotide sequence encoding OmpLA (pldA; b3821; GenBank Ref. NO. NP_418265.1; SEQ ID NO: 4).

By "co-expresses" it is meant that expression of the recombinant protein of interest and the phospholipase is coordinated such that expression of the protein of interest and the phospholipase at least overlap. In some preferred embodiments, expression of the recombinant protein of interest and expression of the phospholipase are under the control of one or more inducible promoters (e.g. on the same or separate expression vectors). In some aspects, expression of the recombinant protein of interest and the phospholipase are under the control of the same inducible promoter (e.g. on the same or separate expression vectors). Expression of the protein of interest and expression of the phospholipase may be induced at about the same time or the protein of interest may be induced prior to the phospholipase or the phospholipase may be induced prior to the protein of interest. In some preferred embodiments, the protein of interest is induced prior to (e.g. between one and six hours prior to) induction of the phospholipase. Preferably, the E. coli phospholipase is overexpressed relative to endogenous levels of the phospholipase and is recombinantly produced (e.g. by introducing into the E. coli an expression vector comprising a nucleotide sequence encoding the phospholipase operably linked to an expression control sequence or by manipulating the promoter of the gene encoding an endogenous phospholipase). Alternatively, an endogenous phospholipase gene may be manipulated to overexpress the phospholipase. Any E. coli phospholipase may be co-expressed with a recombinant protein of interest according to the methods herein described. In some preferred embodiments, the E. coli phospholipase is OmpLA.

In preferred embodiments, a nucleotide sequence encoding a protein of interest and a nucleotide sequence encoding a phospholipase are present in the same construct (e.g. expression vector) and are under the control of the same inducible promoter or are under the control of different inducible promoters. In other embodiments, a nucleic acid segment comprising a nucleotide sequence encoding a protein of interest and a nucleic acid segment comprising a nucleotide sequence encoding an E. coli phospholipase are on separate constructs and under the control of inducible promoters which may or may not be the same.

In several aspects, a method for producing a recombinant protein of interest is provided comprising (i) fermenting a recombinant (e.g. reduced genome) E. coli strain carrying a heterologous nucleic acid comprising (a) nucleotide sequence encoding the recombinant protein of interest fused to sequence targeting the protein of interest to the periplasm operably linked to an expression control sequence and (b) nucleotide sequence encoding an E. coli phospholipase operably linked to an expression control sequence, (ii) inducing expression of the recombinant protein of interest and the phospholipase and (iii) extracting the protein of interest from the periplasm into the medium by contacting the recombinant E. coli strain with an extraction buffer.

In some embodiments, at least 30%, at least 40%, at least 50%, at least 60%, at least 70%, at least 75%, at least 80%, at least 85%, at least 90%, at least 95% or at least 98% of the protein of interest is released from the periplasm according to the methods.

In preferred embodiments, the extraction buffer comprises a buffering agent (e.g. Tris) and a chelating agent (e.g. EDTA) at a pH value of about 7 to 9. In some embodiments, the chelating agent is selected from the group comprising ethylenediaminetetraacetic acid (EDTA), ethylendiamine, nitrilotriacetic acid (NTA), ethylene glycol tetraacetic acid (EGTA), diethylene triamine pentaacetic acid (DTPA), 1,2-bis(o-aminophenoxy)ethane-N,N,N',N'-tetraacetic acid (BAPTA), Ethylenediamine-N,N'-disuccinic acid (EDDS), ethylenediamine tetra(methylene phosphonic acid) (EDTMP) and diethylenetriamine penta(methylene phosphonic acid) (DTPMP). In a preferred embodiment the chelating agent is EDTA. In particularly preferred embodiments, the extraction buffer comprises between 50 and 200 mM Tris, preferably about 150 mM Tris and between 2 mM and 10 mM ethylenediaminetetraacetic acid (EDTA), preferably about 5 mM EDTA, at pH of about 7 to about 9,
preferably about pH 7.75. In some embodiments, extracting the protein of interest from the periplasm into the medium is achieved by contacting the recombinant E. coli with an extraction buffer for at least 2 hours, at least 3 hours, at least 4 hours, at least 6 hours, at least 8 hours, at least 10 hours, at least 12 hours, at least 13 hours, at least 14 hours, at least 15 hours, at least 16 hours, at least 18 hours, at least 20 hours, at least 24 hours or more or any range there between (e.g. between 10 and 20 hours or between 12 and 16 hours). Preferably, the recombinant E. coli is contacted with an extraction buffer for at least 2 and not more than 24 hours, more preferably at least 6 and not more than 24 hours. Preferably, the contacting step occurs at 20-30° C., more preferably about 25° C.

In some embodiments, the method comprises batch fermentation. In other embodiments, the method comprises fed-batch fermentation. In preferred embodiments, the method comprises continuous fermentation. In a particularly preferred embodiment, the method comprises continuous fermentation of a reduced genome strain E. coli. It has been discovered that reduced genome E. coli comprising genomic deletions from about 5% to about 30% can be continuously fermented for periods of at least 7 or more days, at least 14 or more days, at least 21 or more days, at least 30 or more days, at least 45 or more days, at least 60 or more days, at least 180 or more days, at least 240 or more days and even at least 360 or more days or any range there between. In contrast, E. coli strains generally used for fermentation are subject to stress-induced systems that precludes their use in continuous manufacturing. In some embodiments, continuous fermentation methods comprise a two vessel chemostat strategy that separates the growth of a seed culture from an induction phase. Briefly, newly grown cells from an uninduced seed vessel (bio-reactor 1) are fed into a production vessel (bio-reactor 2) where inducer is added and product synthesis initiated. The steady state chemostat, comprising an uninduced seed vessel which provides a supply of healthy cells to the production vessel for induction, ensuring that seed cell growth is stress-free until introduction into the production vessel. Exemplary continuous fermentation apparatus include the apparatus illustrated at FIG. 17 and those described in U.S. Patent Publication No. 20180087018, the contents of which are incorporated herein by reference, although any suitable continuous fermentation method and apparatus may be used to carry out the methods herein described.

A reduced genome E. coli strain comprising a nucleic acid segment encoding a protein of interest fused to a periplasmic targeting signal and co-expressing a phospholipase can be continuously fermented for 7 or more days, for 14 or more days, for 30 or more days, for 45 or more days, for 60 or more days, for 180 or more days, for 240 or more days or even for 360 or more days. In preferred embodiments, a reduced genome E. coli strain comprising a nucleic acid segment encoding a carrier protein selected from CRM197, PD and EPA and co-expressing a phospholipase is continuously fermented for a period of at least 5-65 days (or any range there between) whereby a yield of at least 1-9 grams/liter/day of the carrier protein is obtained in the culture medium during the continuous fermentation. Carrier protein can be purified directly from the culture medium because the E. coli host cells remain intact during the continuous fermentation process and the medium remains substantially free of contaminating cellular protein and nucleic acid resulting from cell lysis.

In other embodiments, genetically modified E. coli strains with improved characteristics are provided that are particularly useful for enhanced expression of difficult-to-produce recombinant proteins such as single-chain antibody fragment scFab YMF10, single-chain antibody variable fragment scFv 75127, the conjugate carrier proteins CRM197, PD, and EPA and that facilitate recovery of these proteins from fermentations.

In several embodiments, an *E. coli* K-12 or B strain is provided comprising deletion(s) of one or more toxin-antitoxin (TA) genes. In some embodiments, the *E. coli* K-12 or B strain comprises chromosomal deletion(s) of one or more TA genes. In other embodiments, the *E. coli* K-12 or B strain comprises deletion(s) of one or more TA genes from a plasmid. In preferred embodiments, the *E. coli* K-12 or B strain does not comprise any chromosomal or plasmid TA genes. In some embodiments, a wild type *E. coli* K-12 or B strain is modified to delete one or more TA genes. In other embodiments, a reduced genome *E. coli* K-12 or B strain (e.g. an *E. coli* K-12 strain that has been genetically modified to be from about 5% to about 30% smaller than the genome of its native parent *E. coli* K-12 strain) is modified to delete one or more TA genes.

The TA genes deleted from the *E. coli* K-12 or B strain may be a Type 1 (e.g. ldrA, rdlA, ldrB, rdlB, ldrC, rdlC, ldrD, rdlD, hokB, sokB, sibA, ibsA, sibB, ibsB, ohsC, shoB, sibC, ibsC, sibD, ibsD, dinQ, agrA, agrB, yhjJ, yhjM, yhjN, istR-2, tisB), Type 2 (e.g. YafQ, dinJ, hha, tomB, gnsA, ymcE, yoeB, yefM, mazF, mazE, mazG, cptA/ygfX, cptB/sdhE, mqsR, mqsA, higB, higA, yhaV, prlF, ldrD, rdlD, istR-2, tisB, chpB, chpS, ratA, ratB, ecnA, ecnB), Type 4 (e.g. cbtA, cbeA), and/or Type 5 (e.g. ghoT, ghoS) TA gene.

In some embodiments one or more and preferably all of the following TA genes are deleted from the *E. coli* strain: YafQ, dinJ, hha, tomB, gnsA, ymcE, yoeB, yefM, mazF, mazE, mazG, cptA/ygfX, cptB/sdhE, mqsR, mqsA, higB, higA, yhaV, prlF, ldrD, rdlD, istR-2, tisB, chpB, chpS, ratA, ratB, ldrA, rdlA, ldrB, rdlB, ldrC, rdlC, hokB, sokB, sibA, ibsA, sibB, ibsB, ohsC, shoB, sibC, ibsC, sibD, sibE, ibsD, ibsE, dinQ, agrA, agrB, ghoT, ghoS, yfeC, yfeD, fic, yhfG, yhjJ, yhjM, yhjN, yjjJ, ecnA, and/or ecnB. In some embodiments, hipA and/or hipB are deleted.

In another embodiment, one or more of the TA genes listed in Table 1 below is deleted from the *E. coli* strain. In preferred embodiments, all Type II TA genes listed in Table 1 are deleted. In particularly preferred embodiments, all TA genes listed in Table 1 are deleted.

TABLE 1

| Toxin/Antoxin gene (b-number) | Type |
|---|---|
| YafQ (b0225) | II |
| dinJ (b0226) | |
| hha (b0460) | II |
| tomB (b0461) | |
| grisA (b0991) | II |
| ymcE (b4517) | |
| ldrA (b4419) | I |
| ldrB (b4421) | |
| ldrC (b4423) | |
| rdlA (b4420) | |
| rdlB (b4422) | |
| rdlC (b4424) | |
| hokB (b4428) | I |
| sokB (b4429) | |
| yoeB (b4539) | II |
| yefM (b2017) | |
| sibA (b4436) | I |
| sibB (b4437) | |
| ibsA (b4667) | |

TABLE 1-continued

| Toxin/Antoxin gene (b-number) | Type |
|---|---|
| ibsB (b4668) | |
| yfeC (b2398) | |
| yfeD (b2399) | |
| ohsC (b4608) | I |
| shoB (b4687) | |
| mazF (b2782) | II |
| mazE (b2783) | |
| mazG (b2781) | |
| cptA (aka ygfX) (b2896) | II |
| cptB (aka sdhE) (b2897) | II / I |
| sibC (b4446) | |
| ibsC (b4665) | I |
| mqsR (b3022) | II |
| mqsA (b3021) | II |
| sibD (b4447) | I |
| sibE (b4611) | |
| ibsD (b4664) | I |
| ibsE (b4666) | II |
| higB (b3083) | |
| higA (b3082) | II |
| yhaV (b3130) | II |
| prlF (b3129) | II |
| fic (b3361) | |
| yhfG (b3362) | I |
| dinQ (b4613) | |
| agrA (b4712) | 1 |
| agrB (b4713) | |
| yhjJ (b3527) | |
| yhjM (b3531) | I |
| yhjN (b3532) | |
| ldrD (b4453) | |
| rdlD (b4454) | I |
| istR-2 (b4616) | I |
| tisB (b4618) | I |
| ghoT (b4559) | V |
| ghoS (b4128) | V |
| ecnA (b4410) | |
| ecnB (b4411) | II |
| chpB (b4225) | |
| chpS (b4224) | II |
| yjjJ (b4385) | |
| ratA (b2619) | II |
| ratB (aka yfjF) (b2618) | II |
| hipA (b1507) | In process of |
| hipB (b1508) | deleting |

In other embodiments, an *E. coli* K-12 or B strain is provided that has been genetically modified to reduce or eliminate expression of the rnc (b2567) gene (encoding ribonuclease III). Preferably, expression of the rnc gene product is reduced or eliminated by partial or full deletion of the rnc gene. In some embodiments, a wild type *E. coli* K-12 or B strain is modified to reduce or eliminate expression of the rnc gene. In preferred embodiments, a reduced genome *E. coli* K-12 strain (e.g. an *E. coli* strain that has been genetically modified to be from about 2% or about 5% to about 22% or about 30% smaller than the genome of its native parent *E. coli* K-12 strain) is modified to reduce or eliminate expression of the rnc gene.

In some embodiments, an *E. coli* K-12 or B strain is provided that comprises a partial or full deletion of the rnc gene and comprises deletions of one or more, and preferably all, of the TA genes listed in Table 1. In preferred embodiments, a reduced genome *E. coli* K-12 strain comprising a partial or full deletion of the rnc gene and deletion of one or more, and preferably all, of the TA genes listed in Table 1 is provided.

In other embodiments, an *E. coli* K-12 strain is provided comprising a partial or full deletion of the rnc gene and/or comprising deletions of one or more, and preferably all, of the TA genes listed in Table 1 and further comprising the following modifications: (a) enhanced orotate phosphoribosyltransferase activity, (b) production of active acetohydroxy acid synthase II and, (c) reduced expression of the iclR and arpA genes.

In related embodiments, an *E. coli* K-12 or B strain is provided comprising a partial or full deletion of the rnc gene and/or comprising deletions of one or more, and preferably all, of the TA gene pairs listed in Table 1 and/or comprising the following modifications: (a) enhanced orotate phosphoribosyltransferase activity, (b) production of active acetohydroxy acid synthase II, and (c) reduced expression of the iclR and arpA genes and comprising a non-functional dinB (b0231, coordinates 250898-251953 on the MG1655 genome) gene and optionally comprising non-functional polB (b0060, coordinates 63429-65780 on the *E. coli* K12 MG1655 genome) and/or umuDC genes (b1183-b1184, coordinates 1229990-1231667 on the MG1655 genome) as described in WIPO Publication No. 2013/059595, the contents of which are incorporated herein by reference. Preferably, the gene(s) are rendered inactive by complete or partial deletion.

In some aspects, a reduced genome *E. coli* K-12 or B strain is provided having a genome that is genetically engineered to be from about 2% or about 5% to about 22% or about 30% smaller than the genome of its native parent strain wherein the reduced genome *E. coli* comprises one or more of the deletions or modifications as herein described and does not comprise insertion sequences.

Reduced genome bacteria may be produced by deleting selected genes from a native parental strain of a bacterium or may, for example, be entirely synthesized as an assembly of preselected genes. As is readily apparent from the discussion herein, a reduced genome bacterium has fewer than the full complement of genes found in a native parent strain to which it is compared, and with which it shares certain essential genes.

Methods for producing a polypeptide of interest employing the modified *E. coli* K-12 or B strains of the invention are also provided in which a soluble polypeptide of interest is targeted to the periplasm and/or is secreted into the fermentation medium. In one embodiment, the polypeptide is produced by culturing the modified *E. coli* K-12 or B strain comprising a nucleic acid encoding the polypeptide operatively linked to an expression control sequence, under conditions suitable to express the polypeptide. In one aspect, the nucleic acid encodes a heterologous protein. In a related aspect, the protein is produced in the modified *E. coli* strains of the invention at a higher level than in an *E. coli* K-12 or B strain that does not comprise the modifications described herein. In still another aspect protein production is increased at a higher level than from an *E. coli* K-12 or B strain that does not comprise the modifications described herein by virtue of the higher cell numbers such modified cells can attain under the same growth conditions. In some embodiments, a modified *E. coli* K-12 or B strain as herein described and carrying a heterologous nucleic acid comprising a nucleotide sequence encoding a protein of interest fused to a periplasmic signal peptide, the nucleotide sequence operably linked to an expression control sequence, and optionally co-expressing an *E. coli* phospholipase, is subjected to continuous fermentation whereby yields of at least 1, at least 2, at least 5, at least 7, and even at least 10 grams/liter/day are obtainable directly from the periplasm (e.g. if a phospholipase is not co-expressed) and/or culture medium (if a phospholipase is co-expressed) for a period of at least one day, at least two days, at least 3 days, at least 4 days, at least 7 days, at least 14 days, at least 30 days, at least 60 days, at least 90 days, at least 120 days, or even at least 365 days.

Methods for amplifying heterologous nucleic acids (e.g. a vector such as plasmid) employing the modified *E. coli* K-12 or B strains of the invention are also provided. In one embodiment, the nucleic acid is produced by culturing the modified *E. coli* K-12 or B strain comprising the heterologous nucleic acid under suitable nutrient conditions, thereby amplifying the nucleic acid. In still another aspect nucleic acid production is increased at a higher level than from an *E. coli* K-12 or B strain that does not comprise the modifications described herein by virtue of the higher cell numbers such modified cells can attain under the same growth conditions.

DESCRIPTION OF THE DRAWINGS

FIGS. 3A-C. Protein D is released into the medium during continuous fermentation. Three separate continuous fermentations (FIGS. 3A, 3B and 3C) were implemented using strain SG69meta (aka MDS69meta) that expressed periplasmic-targeted PD. Induction (100 μM IPTG) was at day 1 in FIG. 3A and FIG. 3B and day 0 in FIG. 3C. Periplasmic PD (dark) and released PD (light) values were measured twice daily using Caliper Labchip capillary protein electrophoresis. Periplasmic PD values (g/L/day) are based on (Moo measurements (average OD for A-C were 224, 220 and 214, respectively). Released PD (light) was measured directly from the medium. Inset in FIG. 3B shows an increase in released PD within the days indicated (Caliper analysis, top of panel). Capillary Western analysis (Wes Instrument, Protein Simple, San Jose, CA) (bottom panel in FIG. 3B) verified the presence of PD in medium samples. Note that Western samples were diluted to obtain measurements that were within the linear range of the instrument. Lines of best fit in FIGS. 3B and 3C (very light) are $4^{th}$ order polynomials.

FIGS. 6A-B illustrate embodiments of the invention. FIG. 6A: The sequence of the intervening junction between the C-Terminus of the CRM197 ORF and pldA ORF is shown. Part A: The original plasmid for expression of CRM197 and two derivative constructs that create a bicistronic expression unit of CRM197 and pldA are shown (SEQ ID Nos:7-9). The stop codon of the CRM197 ORF is followed soon after by a ribosome binding site (RBS) and the pldA ORF. Two representative ribosome binding sites of different strength are shown. Based on the literature and previous experience with other bicistronic constructs, modification of the RBS can be used to increase or decrease the translation frequency of the downstream pldA ORF. Part B: The genome of MDS69meta (aka T69meta) was modified to allow DOX induction of endogenous genomic pldA. The tet Repressor and T5DE20-Dual tetO promoter/operator was inserted upstream of the native pldA gene and its native promoter. The pldA gene of this strain can be induced from its endogenous promoter and from the introduced promoter. FIG. 6B: Expression of PldA from the genome enhanced CRM197 extraction by Tris/EDTA, but did not result in 100% extraction of what is in the periplasm. The inventors have also achieved good results by (i) placing the pldA ORF under the control of a tet-Operator/tet-repressor controlled promoter on a plasmid compatible with pSX2-ytfQ-CRM197 in which OmpLA expression was controlled by the inducer doxycycline in a dose dependent fashion and CRM197 expression was controlled by the inducer IPTG and (ii) placing CRM197 under a tet-Operator/tet-repressor controlled promoter and placing pldA expression under an ITPG-inducible promoter.

FIG. 7 illustrates the effect of co-expression of a phospholipase (PldA is exemplified) on release of recombinant CRM917 into the medium in reduced genome E. coli strain T69 Meta recA (aka MDS69meta recA) carrying a single plasmid expression vector encoding CRM197 fused to a YtfQ secretion signal (under the control of an IPTG-inducible promoter) and encoding OmpLA under the control of a doxycycline-inducible promoter. CRM197 and OmpLA were expressed once host cells reached saturation in shake flask culture and yield of soluble CRM197 in the medium and periplasm was assessed following a 2 hour or overnight incubation with Tris/EDTA. T69 (aka MDS69), is a multiple deletion strain which comprises all the deletions of MDS42 and twenty-seven additional deletions. T69 Meta recA (aka MDS69meta recA) comprises the deletions of MDS69 and also comprises correction of the native rph and ilvG frameshift mutations, deletion of the iclR and arpA genes and deletion of the recA gene.

FIG. 8 illustrates the effect of co-expression of a phospholipase (OmpLA is exemplified) on release of recombinant Exoprotein A (rEPA) into the medium in reduced genome E. coli strain T69 Meta recA (aka MDS69meta recA) carrying a single plasmid expression vector encoding rEPA fused to a YtfQ secretion signal (under the control of an IPTG-inducible promoter) and encoding OmpLA under the control of a doxycycline-inducible promoter. rEPA and OmpLA were induced once host cells reached saturation in shake flask culture and yield of soluble rEPA in the medium and periplasm was assessed following a 2 hour or overnight incubation with Tris/EDTA.

FIGS. 12A-D. FIG. 12A shows CRM197 yield in the periplasm (Epicentre periplasmic prep method with lysozyme) in strain T69 Meta Tox/Atox LowMut recA (aka MDS69meta T/A LowMut recA) (i) carrying an expression plasmid encoding CRM197 fused to a YtfQ secretion signal under the control of a doxycycline-inducible promoter or carrying a bicistronic expression plasmid encoding CRM197-ytfQ and pldA (codon optimized) with either of two ribosome binding sites (see FIG. 6) between the CRM197 and pldA orfs. FIG. 12B is the same culture as in FIG. 12A, but instead of the Epicentre Peri prep with lysozyme, one ml of the induced culture was subjected to overnight shaking at 25° C. (no Tris/EDTA treatment). In the presence of OmpLA, ~5× more target protein goes into the media from the periplasm with just shaking at 25° C. (which is still only 50% of the total amount of target protein extracted into the media with OmpLA and Tris/EDTA treatment). FIG. 12C illustrates CRM197 yield in the media following induction of pldA expression and extraction with Tris/EDTA and shaking at 25° C. The left most panel shows that very little target is extracted from the periplasm to the media, whereas the right two panels produce on average 5× more extracted to media relative to the left panel. In the right two panels there is on average 2× more extracted CRM197 than the same two panels in FIG. 12B. FIG. 12D shows pldA expression and incubation of a one ml sample of induced culture at 4° C. for two days. Incubation at 4° C. (without Tris/EDTA) vs. 25° C. (without Tris/EDTA) does not improve "leakage" of target from periplasm into media.

FIG. 18 compares periplasmic yield of CRM197 in T69 Meta recA (aka MDS69meta recA), T69 Meta recA T/AT (aka MDS69meta T/A recA) and T69 Meta recA T/AT LowMut (aka MDS69meta T/A LowMut recA) host cells carrying an expression plasmid encoding CRM197 fused to a YtfQ secretion signal under the control of a doxycycline-inducible promoter. Deletion of the toxin/antitoxin genes significantly enhances the yield of CRM197 in the periplasm.

FIG. 19A: periplasmic and extracted yield of scFv 75127 is shown following induction of scFv and pldA expression in reduced genome E. coli strain SG69meta (aka T69 Meta aka MDS69meta) containing a dual scFv, pldA bicistronic expression plasmid construct. FIG. 19B: periplasmic and extracted yield of scFab YMF10 is shown following induction of scFv and OmpLA expression in reduced genome E. coli strain SG69meta (aka T69 Meta aka MDS69meta) containing a dual scFab, pldA bicistronic expression plasmid construct.

FIGS. 20A-B illustrate periplasmic (FIG. 20A) and extracted yield (FIG. 20B) of scFv 75127 in MDS69meta recA (aka T69 Meta recA) and MDS69meta T/AT LowMut RecA (aka T69 Meta T/AT LowMut recA) strain carrying an expression plasmid encoding the scFv fused to an OmpA secretion signal under the control of an IPTG-inducible promoter and pldA under the control of a DOX-inducible promoter. scFv expression was induced and four hours later expression of pldA was induced and induction continued overnight at which time cells were contacted with Tris/EDTA extraction buffer (as described above) overnight at 25° C.

Figure 22:
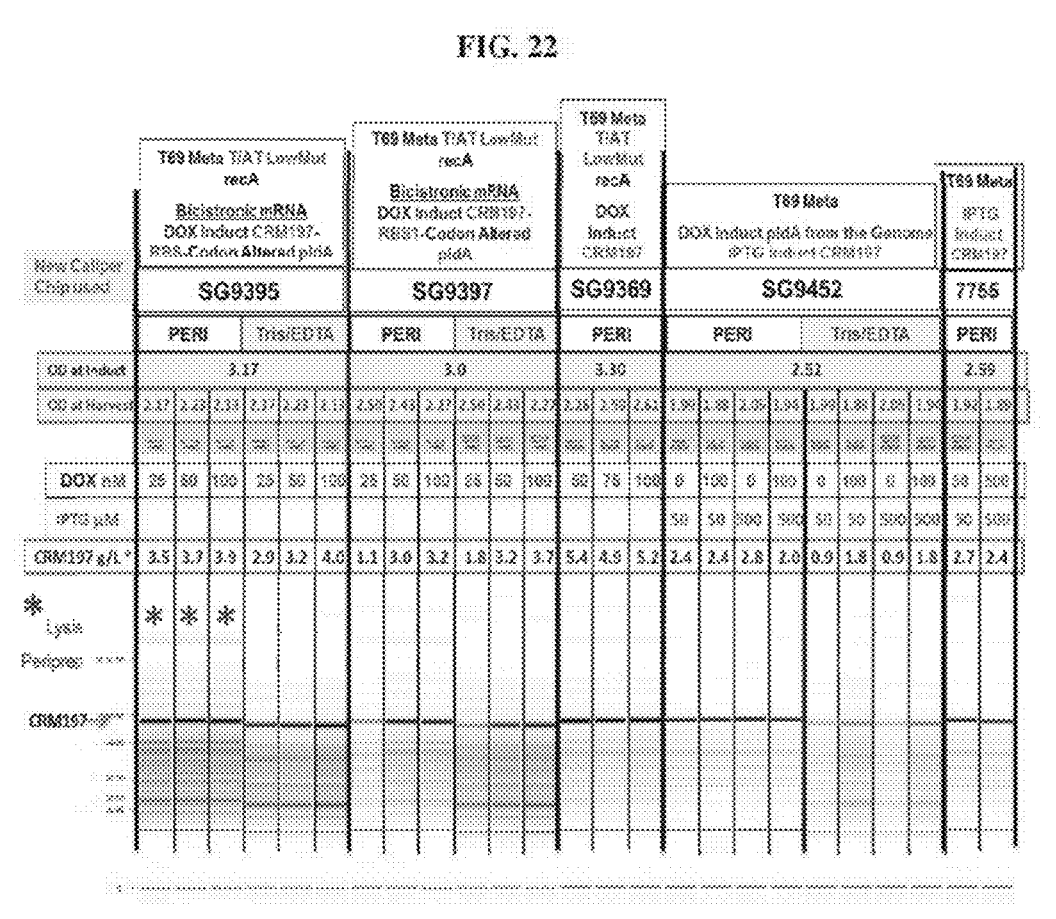

FIG. 22 illustrates periplasmic yield of CRM197 and CRM197 yield following Tris/EDTA extraction in MDS69meta T/AT LowMut recA and MDS69meta strains

DETAILED DESCRIPTION OF THE INVENTION

Figure 1:
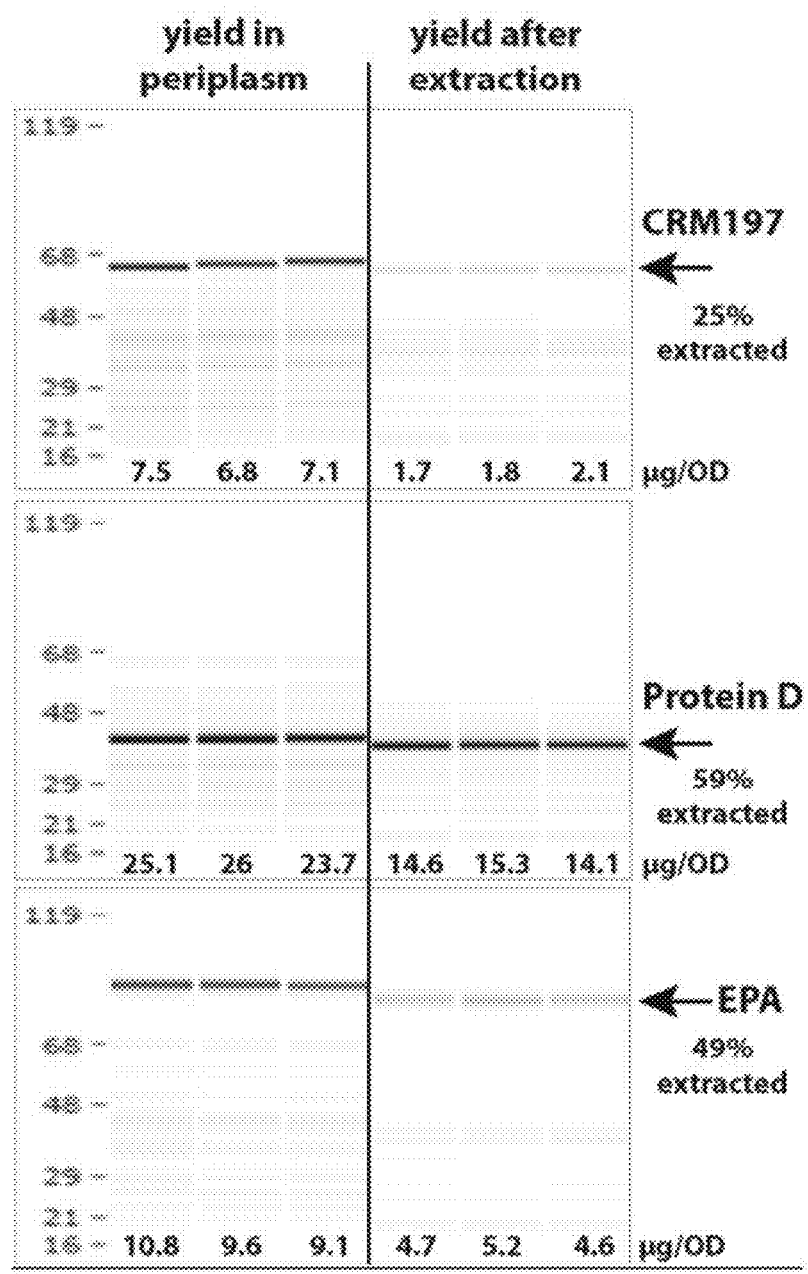
FIG. 1. Extraction of Carrier Proteins in Shake Flask Culture. Periplasmic yields of CRM197, Protein D and EPA (left panels) were compared to yields obtained using an extraction buffer (150 mM Tris pH 7.75, 5 mM EDTA) (right panels). Briefly, in each case, a reduced genome *E. coli* strain carrying an expression plasmid encoding the carrier protein fused to a secretion signal (e.g. YtfQ) was subjected to shake flask culture and the carrier protein was induced once the host cells reached saturation. The percent of periplasmic yield for each carrier protein is shown following 6 hour incubation with Tris/EDTA extraction buffer. Protein yields from triplicate experiments are shown in each case.

The inventors have discovered that recombinant therapeutic proteins, including but not limited to single-chain antibody fragment scFab YMF10, single-chain antibody variable fragment scFv 75127, CRM197, Protein D and EPA, delivered into the cell periplasm of E. coli host cells that co-express an endogenous E. coli phospholipase, can be extracted directly into the culture medium during fermentations, reducing production time and effort, greatly simplifying purification of these proteins and dramatically reducing production costs.

Use of the methods and compositions herein described overcome several standard manufacturing challenges associated with CRM197 and other carrier proteins including: (1) low levels of CRM197 (0.1 to 0.2 g/L) in the original Corynebacterium diphtheria host (2) potential reversion of CRM197 to wild type toxin in alternative hosts such as Pseudomonas fluorescens and many E. coli strains (3) physiological stress in fermentation hosts under high production rates of CRM197 (4) accumulation of CRM197 in an insoluble form in most E. coli hosts, reducing yield and significantly complicating downstream purification steps (5) activation of cryptic prophage or insertion elements, or disruption of toxin/anti-toxin homeostasis and other mutation-generating, stress-induced systems in *E. coli* host cells that can induce cell lysis and compromise the use of these strains in continuous manufacturing.

Using the reduced genome *E. coli* strains and methods described herein, the inventors have discovered and verified that periplasmic-targeted proteins such as CRM197, PD and EPA can be continually produced and extracted from the cells directly into the culture medium for easy purification at high yields (over 3 g per liter per day) which can be maintained for periods of at least 30 days and even at least 65 days or more during continuous fermentation. In contrast, conventional *E. coli* strains are unable to sustain production for more than a few days under the same conditions.

CRM197 is a genetically non-toxic form of diphtheria toxin (DT). A single base change (glutamic acid to glycine at position 52) in CRM197 disables the ADP-ribosylation activity of the A chain attenuating toxicity. Although CRM197 is non-toxic, it is immunologically indistinguishable from diphtheria toxin. CRM197 functions as a carrier for polysaccharides and haptens making them immunogenic in several conjugate vaccines.

PD is an immunoglobulin D-binding membrane lipoprotein exposed on the surface of the gram-negative bacterium *Haemophilus influenza*. The protein is synthesized as a precursor with an 18-residue-long signal sequence modified by the covalent attachment of both ester-linked and amide-linked palmitate to a cysteine residue, which becomes the amino terminus of the mature protein after cleavage of the signal sequence. Mutant protein D lacking the cysteine residue is not acylated. The nonacylated protein D molecule localizes to the periplasmic space of *E. coli*. The hydrophilic protein D molecule functions as a carrier for polysaccharides and haptens making them immunogenic in conjugate vaccines.

Carrier protein EPA from *Pseudomonas aeruginosa* activates T cells in the same fashion as CRM197. Because CRM197 is used in so many conjugate vaccines, including the world's best selling vaccine, Prevnar-13, some vaccine producers have chosen to use it to avoid epitope suppression. EPA is used in the nicotine vaccine NicVAX which has been shown to mitigate nicotine dependence (Esterlis I, Hannestad J O, Perkins E, Bois F, D'Souza D C, Tyndale R F, Seibyl J P, Hatsukami D M, Cosgrove K P, O'Malley S S. Effect of a nicotine vaccine on nicotine binding to beta2*-nicotinic acetylcholine receptors in vivo in human tobacco smokers. Am J Psychiatry. 2013; 170(4):399-407. doi:.1176/appi.ajp.2012.12060793. PubMed PMID: 23429725; PMCID: PMC3738000.) Anti-malarial conjugate vaccines using EPA have shown success in development and have entered clinical trials.

The inventors have found that co-expressing *E. coli* phospholipases with a periplasmic-targeted protein of interest in an *E. coli* host cell provides a system in which nearly all of the protein of interest can be extracted into the medium with an appropriate buffer. In preferred embodiments, the phospholipase is selected form the group consisting of GlpQ, YbaC, PldA, PldB and TesA. These exemplary phosphodiesterases are discussed below.

Glycerophosphoryl diester phosphodiesterase (GlpQ) is involved in the utilization of the glycerol moiety of phospholipids and triglycerides after their breakdown into usable forms such as glycerophosphodiesters, sn-glycerol-3-phosphate (G3P) or glycerol. GlpQ catalyzes the hydrolysis of glycerophosphodiesters into sn-glycerol 3-phosphate (glycerol-P) and an alcohol. The glycerol-P is then transported into the cell by the glycerol-P transporter, GlpT. Periplasmic GlpQ is specific for the glycerophospho-moiety of the substrate, but the alcohol can be any one of several long and medium-chain alcohols. This provides the cell with the capability of channeling a wide variety of glycerophosphodiesters into the glp-encoded dissimilatory system. In some embodiments, an *E. coli* host cell, preferably a reduced genome *E. coli* host cell, for use in the methods herein described comprises a nucleic acid segment comprising nucleotide sequence encoding a polypeptide of SEQ ID NO: 1 or a sequence at least 80%, at least 85%, at least 90%, at least 95%, at least 98%, or at least 99% identical thereto.

Aes (encoded by the ybaC gene) catalyzes hydrolysis of p-nitrophenyl esters of fatty acids, preferring substrates with short (<8 in length) acyl chains. Aes has structural similarity to lipases and esterases and belongs to the hormone-sensitive lipase (HSL) protein family. The enzyme may be either monomeric or homodimeric; it has been crystallized, and crystal structures have been solved. Denaturant-induced unfolding of the enzyme has been studied, and a mutant with higher thermostability has been isolated. The catalytic triad was predicted to comprise ser165, asp262, and his292; site-directed mutagenesis confirmed that these residues are required for catalytic activity. In addition, asp164 is thought to be structurally important. Point mutations in l97 and l209 increase enzymatic activity by increasing $k_{cat}$ and decreasing $k_m$, respectively. Overexpression of aes results in increased p-nitrophenyl acetate hydrolysis, compared to wild type. In some embodiments, an *E. coli* host cell, preferably a reduced genome *E. coli* host cell, for use in the methods herein described comprises a nucleic acid segment comprising a nucleotide sequence encoding a polypeptide of SEQ ID NO: 2 or a sequence at least 80%, at least 85%, at least 90%, at least 95%, at least 98%, or at least 99% identical thereto.

*E. coli* K-12 gene pldA encodes the outer membrane phospholipase A (OmpLA) protein. Purified OmpLA displays multiple lipolytic activities and is active on phospholipids, lysophosphospholipids, diglycerides and monoglycerides however in vivo the expected substrates are the phospholipids of the cell envelope. Dimerization of OmpLA is necessary for phospholipase activity. Interactions between enzyme and the substrates acyl side chains are the predominant stabilizing factor in dimerization. Although pldA is constitutively expressed, OmpLA activity is not detected under normal conditions but is induced by conditions which disturb outer membrane integrity. OmpLA has been implicated in bacteriocin release.

In *E. coli* strains containing a colicin producing plasmid the activity of OmpLA increased prior to lysis and bacteriocin release, and phosphatidylethanolamine (the major bacterial outer membrane phospholipid) was degraded. In a colicin producing *E. coli* pldA mutant, colicin is retained in the cytoplasm. In some preferred embodiments, an *E. coli* host cell, preferably a reduced genome *E. coli* host cell, for use in the methods herein described comprises a nucleic acid segment comprising a nucleotide sequence encoding a polypeptide of SEQ ID NO: 4 or a sequence at least 80%, at least 85%, at least 90%, at least 95%, at least 98%, or at least 99% identical thereto.

Lysophospholipase L2 (PldB) hydrolyzes the bond to the remaining acyl group of lysophospholipids. The most effective substrates are 2-acyl glycerophosphoethanolamine and 2-acyl glycerophosphocholine; the 1-acyl versions of each compound are hydrolyzed somewhat less effectively. In addition, PldB can transfer an acyl group from certain lysophospholipids to phosphatidylglycerol to yield acyl phosphatidylglycerol. PldB does not contain an obvious signal sequence or transmembrane domain and is thought to be associated with the cytoplasmic side of the inner membrane. In some embodiments, an *E. coli* host cell, preferably a reduced genome *E. coli* host cell, for use in the methods herein described comprises a nucleic acid segment comprising a nucleotide sequence encoding a polypeptide of SEQ ID NO: 3 or a sequence at least 80%, at least 85%, at least 90%, at least 95%, at least 98%, or at least 99% identical thereto.

The TAP complex (TesA) is a broad-specificity esterase that carries out thioesterase, arylesterase, lysophospholipase, and protease activities. Its exact function within the cell is unclear, and may potentially involve generating free fatty acids or salvaging compounds containing ester linkages. TesA (pldC; b0494; GenBank Ref. No. NP_416742.1; SEQ ID NO: 5) is a multifunctional esterase that can act as a thioesterase, arylesterase, lysophospholipase, and has limited protease activity. It acts as a thioesterase on a very wide range of acyl-CoA molecules, although it has been reported to be specific for fatty acyl thioesters of greater than ten carbons, with highest activity on palmityl, palmitoleyl, and cis-vaccenyl esters. The actual in vivo role of TesA is unclear. Its location in the periplasm largely precludes access to fatty acyl-CoA molecules. In some embodiments, an *E. coli* host cell, preferably a reduced genome *E. coli* host cell, for use in the methods herein described comprises a nucleic acid segment comprising a nucleotide sequence encoding a polypeptide of SEQ ID NO: 5 or a sequence at least 80%, at least 85%, at least 90%, at least 95%, at least 98%, or at least 99% identical thereto.

The methods described herein allow extraction of a protein of interest into any *E. coli* host cell. In some embodiments, the *E. coli* host cell according to the methods described herein is a wild type *E. coli* B or K12 strain.

In some preferred embodiments of the invention, a recombinant *E. coli* host strain according to the methods and compositions described herein is a reduced genome bacterium. A "reduced genome" bacterium as used herein means a bacterium having about 1% to about 75% of its genome (e.g. protein coding genes, genes that encode for RNA) deleted, for example about 2%, about 5%, about 10%, about 20%, about 30% about 40%, about 50% or about 60% of the genome deleted. In one embodiment, the reduced genome bacteria used in the practice of the present invention have a genome that is preferably genetically engineered to be at least two percent (2%) and up to thirty percent (30%) (including any number there between) smaller than the genome of a native parent strain. Preferably, the genome is at least two percent (2%) and up to twenty five percent (25%) smaller than the genome of a native parent strain. The genome may be about two percent (2%), five percent (5%), eight percent (8%), fourteen percent (14%), twenty-two percent (22%), twenty-five percent (25%), thirty percent (30%) (including any number there between) or more smaller than the genome of the native parent strain. Alternatively, the genome may be engineered to be less than 10%, less than 15%, less than 20%, less than 25% or less than 30% smaller than the genome of a native parental strain. The reduced genome bacterium may have a genome that is between 4.55 Mb (2%) and 3.25 Mb (30%), between 4.41 Mb (5%) and 3.62 Mb (22%), between 4.41 Mb and 3.25 Mb or between 4.41 Mb and 2.78 Mb. The term "native parental strain" means a bacterial strain found in a natural or native environment as commonly understood by the scientific community to represent the foundation of a strain line and on whose genome a series of deletions can be made to generate a bacterial strain with a smaller genome. Native parent strain also refers to a strain against which the engineered strain is compared and wherein the engineered strain has less than the full complement of the native parent strain. The percentage by which a genome has become smaller after a series of deletions is calculated by dividing "the total number of base pairs deleted after all of the deletions" by "the total number of base pairs in the genome before all of the deletions" and then multiplying by 100. Similarly, the percentage by which the genome is smaller than the native parent strain is calculated by dividing the total number of nucleotides in the strain with the smaller genome (regardless of the process by which it was produced) by the total number of nucleotides in a native parent strain and then multiplying by 100.

In one embodiment, a "reduced genome" bacterium means a bacterium for which removal of the above amounts of genome does not unacceptably affect the ability of the organism to grow on minimal medium. Whether removal of two or more genes "unacceptably affects" the ability of the organism to grow on minimal medium in the present context depends on the specific application and is readily assessed. For example, a 30% reduction in proliferation rate may be acceptable for one application but not another. In addition, adverse effect of deleting a DNA sequence from the genome may be reduced by measures such as changing culture conditions. Such measures may turn an otherwise unacceptable adverse effect to an acceptable one. In one embodiment, the proliferation rate is approximately the same as the parental strain. However, proliferation rates ranging from about 5%, 10%, 15%, 20%, 30%, 40% to about 50% lower than that of the parental strain are within the scope of the invention. More particularly, doubling times of bacteria of the present invention may range from about fifteen minutes to about three hours. Non-limiting examples of suitable reduced genome bacteria, as well as methods for cumulatively deleting genomic DNA from a bacterium such as *E. coli*, are disclosed in U.S. Pat. Nos. 6,989,265, 7,303,906, 8,119,365, 8,039,243, 8,178,339, 8,765,408 and 9,902,965, each of which is hereby incorporated by reference herein.

The parental *E. coli* strain in the context of a reduced genome bacterium may be any *E. coli* strain. In some preferred embodiments, the parental *E. coli* strain is a K-12 strain (e.g. MG1655 (GenBank Accession No. U00096.3), W3110 (GenBank Accession No. AP009048.1), DH10B (GenBank Accession No. CP000948.1), DH1 (GenBank Accession No. CP001637.1), or BW2952 (GenBank Accession No. CP001396.1)). In other embodiments, the parental *E. coli* strain is a B strain (e.g. BLR(DE3) (GenBank Accession No. CP020368.1), REL606 (GenBank Accession No. CP000819.1), BL21(DE3) (GenBank Accession No. CP001509.3)).

In one aspect, the parental *E. coli* strain is a K-12 or B strain lacking one or more of the genes listed at Tables 2-20 of U.S. Pat. No. 8,178,339, the contents of which are incorporated herein by reference.

In some preferred embodiments, a reduced genome *E. coli* K12 or B strain as herein described lacks (e.g. comprises deletions of) at least the following genes of the *E. coli* K-12 strain MG1655 (identified by "b" numbers based on the designations set out in Blattner et al., Science, 277:1453-74 and in GenBank Accession No. U00096.3): b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-b4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 or lacks the corresponding genes on a different K-12 or B strain. These are the genes deleted from parental strain MG1655 to create multiple deletion strain MDS42.

In other preferred embodiments, a reduced genome *E. coli* K12 or B strain as herein described lacks (e.g. comprises deletions of) at least the following genes of the *E. coli* K-12 strain MG1655: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153, b2945, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502 or lacks the corresponding genes on a different K-12 or B strain. These are the genes deleted from parental strain MG1655 to create multiple deletion strain MDS69 (aka T69 aka SG69).

Recombinant bacteria for use in the methods described herein may comprise a functional recA gene (b2699) or may lack a functional recA gene (b2699). For example, a reduced genome *E. coli* strain such as e.g. strain MDS42 or MDS69 (aka T69 or SG69) can be modified by inactivation of b2699 by complete or partial deletion of the gene from the modified *E. coli* K-12 strain.

In some embodiments, a reduced genome *E. coli* for use in the methods described herein comprises one or more of the following deletions/modifications: (i) deletion of one or more toxin-antitoxin genes of Table 1 (ii) a partial or full deletion of the rnc gene encoding RNAse III (iii) a deletion of dinB (iv) the following modifications: (a) enhanced orotate phosphoribosyltransferase activity (b) production of active acetohydroxy acid synthase II and (c) reduced expression of the iclR and arpA genes) and (v) a deletion of the recA gene. In related embodiments, a reduced genome *E. coli* for use in the methods described herein is based on parental *E. coli* K12 strain MG1655 and comprises the deletions of MDS42 or MDS69 (aka T69 or SG69) and one or more of the deletions/modifications listed above.

In other embodiments, a non-naturally occurring *E. coli* bacterium having a genome between 4.41 Mb and 2.78 Mb and lacking the following toxin-antitoxin genes: yafQ, dinJ, hha, tomB, gnsA, ymcE, yoeB, yefid, mazF, mazE, mazG, cptA/ygfX, cptB/sdhE, mqsR, mqsA, higB, higA, yhaV, prlF, ldrD, rdlD, istR-2, tisB, chpB, chpS, ratA, ratB, ldrA, rdlA, ldrB, rdlB, ldrC, rdlC, hokB, sokB, sibA, ibsA, sibB, ibsB, ohsC, shoB, sibC, ibsC, sibD, sibE, ibsD, ibsE, dinQ, agrA, agrB, ghoT, ghoS, yfeC, yfeD, fic, yhfiG, yhjJ, yhjM, yhjN, yjjJ, ecnA, and ecnB and/or lacking a functional rnc gene. In related embodiments, the non-naturally occurring *E. coli* bacterium additionally lacks all IS1, IS2, IS3, IS5, IS 150 and IS186 insertion sequences.

EXAMPLES

The following examples illustrate the scope of the invention. Specific elements of the examples are for descriptive purposes only and are not intended to limit the scope of the invention. Those skilled in the art could develop equivalent methods and utilize comparable materials that are within the scope of the invention.

Strains used in the Examples below are as follows:

Strain "MDS69" (aka SG69 or T69) is a reduced genome *E. coli* K12 strain, the native parent of which is MG1655, and which lacks the following genes of MG1655: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153, b2945, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502.

Strain "MDS69meta" (aka SG69 meta or T69 meta) lacks the genes described above for strain MDS69 and further comprises the following (meta) modifications: correction of the native rph and ilvG frameshift mutations and deletion of the iclR and arpA genes.

Strain "MDS69meta recA" (aka SG69 meta recA or T69 meta recA) lacks the genes and comprises the modifications described above for strain MDS69meta and further comprises a deletion of the recA gene.

Strain "MDS69meta T/A recA" (aka SG69 meta T/A recA or T69 meta T/A recA) lacks the genes and comprises the modifications described above for strain MDS69meta recA and further lacks the following toxin/antitoxin genes: YafQ, dinJ, hha, tomB, gnsA, ymcE, yoeB, yefM, mazF, mazE, mazG, cptA/ygfX, cptB/sdhE, mqsR, mqsA, higB, higA, yhaV, prlF, ldrD, rdlD, istR-2, tisB, chpB, chpS, ratA, rata, ldrA, rdlA, ldrB, rdlB, ldrC, rdlC, hokB, sokB, sibA, ibsA, sibB, ibsB, ohsC, shoB, sibC, ibsC, sibD, sibE, ibsD, ibsE, dinQ, agrA, agrB, ghoT, ghoS, yfeC, yfeD, fic, yhfG, yhjJ, yhjM, yhjN, yjjJ, ecnA, and ecnB.

Strain "MDS69meta T/A LowMut recA" (aka SG69 meta T/A LowMut recA or T69 meta T/A LowMut recA) lacks the genes and comprises the modifications described for strain MDS69meta T/A recA and further comprises a deletion of the dinB gene.

All of the above MDS strains are insertion sequence-free.

Example 1

Buffer Extraction of Recombinant Carrier Proteins in a Reduced Genome Strain

Methods to extract recombinant proteins from the periplasm of *E. coli* are common at small scale. However, lab-scale periplasmic isolation methods use osmotic pressure and expensive enzymes or organic solvents that cannot be easily or cheaply used at an industrial scale. Considerable time and effort was spent by the inventors to develop an economical method for periplasm extraction that is scalable.

After testing numerous buffer systems, detergents, and enzymes in combination, an extraction buffer comprising Tris-HCl and EDTA (final conditions=150 mM Tris pH 7.75, 5 mM EDTA) was identified that is capable of extracting recombinant proteins from the periplasm of *E. coli* strains (reduced genome *E. coli* strains are exemplified). Compared to standard Epicentre periplasmic isolation method, this buffer was able to extract 25%, 59% and 49% of CRM197, Protein D and EPA, respectively (see FIG. 1).

Example 2

Deletion of Murein Lipoprotein Gene

Although results with the extraction buffer were encouraging, genetic methods to enhance the amount of extraction were explored in view of the inconsistency in extraction success between proteins of different classes.

Figure 2:
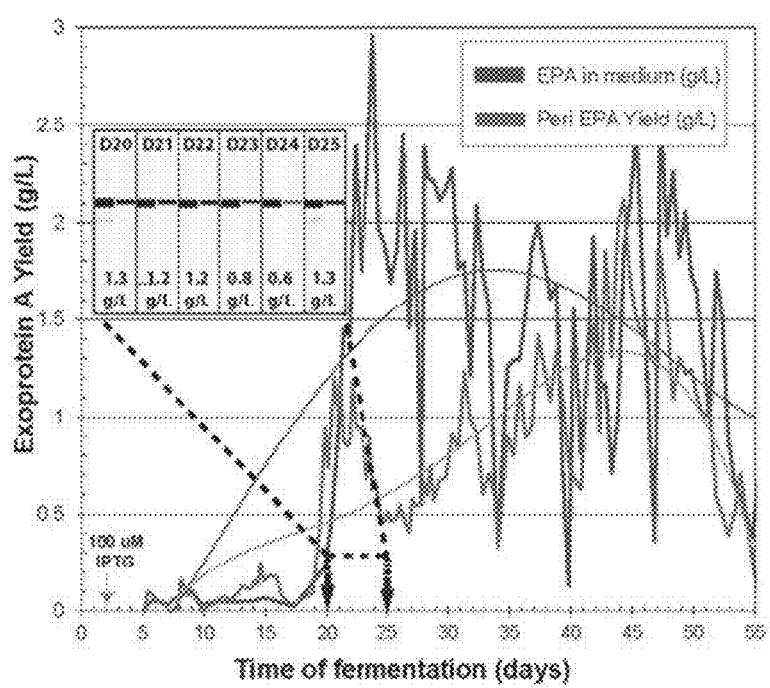
FIG. 2. Strain SG69 meta lpp is capable of releasing EPA into the culture medium which facilitates purification. Continuous fermentation showing EPA expression and release. Note that periplasmic EPA (dark) does not accumulate until 3 weeks post-induction. EPA amounts in the culture medium are shown in light. Lines of best fit in A (thin light and medium) are $4^{th}$ order. Inset: EPA within the culture medium of six one day batches (day 20 to 25, denoted D20-D25) analyzed by capillary Western using polyclonal antibodies to EPA. Duplicate lanes in each instance correspond to 1:10 and 1:100 dilutions.

First, the gene encoding murein lipoprotein (lpp) was removed from *E. coli* strain MDS69meta (aka SG69meta aka T69meta) to create strain MDSmeta Δlpp (aka SG69meta Δlpp aka T69meta Δlpp). Strain MDS69meta is a reduced genome *E. coli* strain based on parental K-12 strain MG1655 and comprises the following deletions relative to MG1655: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153, b2945, b0315-b0331, b0333-b0341, b0346-b0354, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502 (the genes deleted from MG1655 to create MDS69 (aka SG69 or T69) and further comprises the following (meta) modifications: correction of the native rph and ilvG frameshift mutations, deletion of the iclR and arpA genes and deletion of the recA gene. Lpp (Braun's lipoprotein) is a major outer membrane protein that anchors the cytoskeletal-like peptidoglycan layer of the periplasm to the cell envelope and the inactivation of LPP has been found to enhance the release of proteins from the periplasm. However, strain MDS69meta Δlpp was found to be limited in its ability to release proteins from the periplasm and was susceptible to lysis during extended fermentation. Further, the extraction buffer did not cause or enhance the release of recombinant proteins from strain MDS69meta Δlpp (aka SG69meta Δlpp aka T69meta Δlpp) during continuous fermentation. Nevertheless, some release of recombinant proteins was observed. FIG. 2 illustrates a continuous fermentation experiment where the carrier protein EPA (fused to a periplasmic expression sequence) was expressed in strain MDS69meta Δlpp (aka T69meta Δlpp and denoted SG69meta Δlpp on FIG. 2). EPA was released into the culture medium once expression was initiated (FIG. 2). However, expression was low for the first three weeks and the seed and production cultures were found to be susceptible to cell lysis. Once conditions were altered to facilitate more consistent growth, levels of EPA stabilized somewhat, and the culture medium was collected for EPA purification. Production continued for about 35 days, although variations in expression were observed throughout this time due primarily to changes in the amount of cell lysis. For example, cell densities were relatively low throughout the fermentation described in FIG. 2 ($OD_{600}$ values were between 90 and 150 compared to $OD_{600}$ values of between 220 and 270 for fermentations using MDS69meta aka T69meta and SG69meta).

Figure 4:
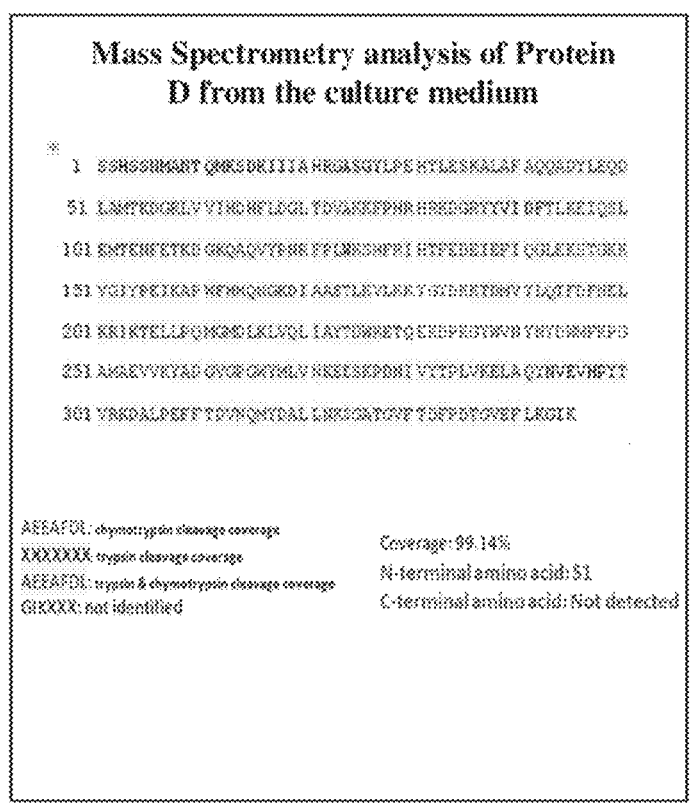
FIG. 4. Verification of PD sequence (SEQ ID NO:6) using mass spectrometry. A highly enriched band from fermentation media corresponding to putative PD was excised from a 4-12% SDS-PAGE slab gel and subjected to either tryptic or chymotryptic digestion followed by mass spectrometry. Coverage was >99%.

The identity of EPA in the culture medium was determined initially using Caliper Labchip (FIG. 2). However, EPA migrated slower on capillary electrophoresis compared to standard SDS PAGE, and identity was therefore confirmed using capillary Westerns with EPA-specific polyclonal antibodies (inset in FIG. 2). Finally, partially purified EPA subjected to MS clearly identified the predicted protein (99% coverage) without modifications or misplaced amino acids (FIG. 4).

The inset in FIG. 2 indicates the concentration of EPA within the culture medium of six one-liter consecutive daily collections. The overall purification process was greatly simplified and EPA was purified to >90% after a single chromatographical purification step again illustrating the advantage of using a recombinant protein released in the culture medium as the first step in protein purification and demonstrating the value of developing a method for extracting proteins into the culture medium.

Although MDS69meta Δlpp (aka T69meta Δlpp and SG69meta Δlpp) released EPA more consistently compared to MDS69meta (aka T69meta and SG69meta), its susceptibility to lysis, likely due to a drastically altered external membrane, limits its application for commercial production of released carrier protein. For example, although MDS69meta Δlpp expressed the carrier protein CRM197 in continuous fermentation (C-Flow), release of CRM197 into the culture medium using MDS69meta Δlpp was never observed. However, intermittent release of moderate amounts of CRM197 into the culture medium in continuous fermentation experiments that used MDS69meta with normal levels of Lpp was observed.

Example 3

Co-Expression with OmpLA Treatment Results in Extraction of Recombinant Proteins The inventors observed that Protein D (PD) of *Haemophilus influenza*, a protective nontypeable *H. influenzae* antigen and a carrier protein for pneumococcal conjugate vaccines, was released at moderate amounts into the medium during continuous fermentation of *E. coli* strain MDS69meta (aka SG69meta aka T69meta) without Tris/EDTA extraction and was removed from the periplasm more effectively than CRM197 and EPA. FIGS. 3A-C illustrate three PD, continuous fermentations in which a transient spike in the release of PD into the culture medium occurred after high levels of PD were observed in the bacterial cell periplasm. Note that levels of PD within the medium were as high as 10 grams per liter, high levels for a released recombinant protein. Intact PD within the medium was confirmed by Caliper LabChip, capillary Westerns using anti-PD antibodies (inset in FIG. 3B), and SDS-PAGE electrophoresis (not shown). Release did not appear to be the result of extensive cell lysis because an increase in cellular protein was not observed in the medium nor was there evidence of an increase in material that results from cell lysis (i.e., nucleic acid). Further, PD was easily purified from the medium with little pretreatment prior to chromatography (see below).

The release of PD did not parallel periplasmic PD concentration. Increased expression of PD later in the fermentation depicted in FIG. 3C did not result in enhanced levels of PD in the medium. That is, periplasmic levels of PD increased from days 25 to 30 in FIG. 3C with no appreciable increase in PD levels in the medium. The absence of PD in the medium during this time was not the result of PD degradation since partially purified PD from a previous fermentation "spiked" into medium samples from day 28 remained intact after 24-hour incubation at 25° C.

To confirm the identity of PD, putative PD in the medium of C-Flow FIG. 1B was separated from contaminating proteins on a 4-12% acrylamide gel, excised from the gel and subjected to mass spectrometry (MS). As shown in FIG. 4, MS identified the excised band as PD. No contaminating proteins were evident in the excised region illustrating the advantage of using culture medium for PD purification (see below). The complete N-terminus of PD (minus the terminal cysteine) was identified as predicted and overall coverage was greater than 99%. Post-translational modifications such as acylation were not evident, as expected.

To identify the mechanism responsible for the release of PD, several culture conditions were modified. One parameter tested, increasing inducer concentration, was postulated to enhance PD in the periplasm and facilitate an increase in movement of PD into the medium. Although an increase in the amount of PD in the periplasm was observed up to the highest inducer concentration examined (300 µM IPTG), little or no PD was evident in the culture medium. To determine whether a stressful event caused PD release, we examined both an increase in temperature and a decrease in pH during PD expression in C-Flow. Neither alteration in fermentation condition resulted in the release of PD into the medium.

The presence of protein D in the periplasm was hypothesized to alter the outer cell membrane by its endogenous glycerophosphodiesterase activity. However, co-induction of Protein D and either CRM197 or EPA did not influence either the release or extraction of CRM197 or EPA in shake-flask culture.

Although the trigger for the release of PD into the culture medium had not yet been identified, a simple purification method for PD was developed using continuous fermentation (aka C-Flow) samples containing released PD. Medium samples that contained high levels of PD (about 10 g/L on day 21, FIG. 3B) were used to develop a purification scheme that required only two chromatography steps to achieve 95% purity. The ease of purification of PD was due directly to the high proportion of PD in the medium (58%). Given the simplicity of the purification protocol, the described method is highly amenable to automation in a continuous end-to-end manufacturing process for recombinant proteins.

Figure 5A:
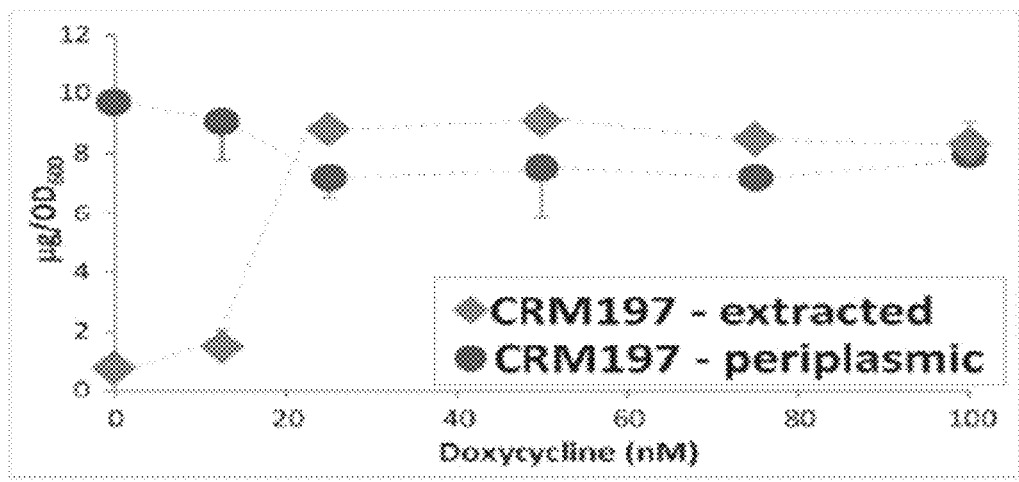
FIGS. 5A-C. Extraction of carrier proteins from shake-flask culture following the expression of pldA. Cultures of host strain SG69meta carrying a plasmid encoding carrier protein fused to a YtfQ secretion signal (under the control of an IPTG-inducible promoter) and pldA (under the control of a doxycycline (DOX)-inducible promoter) were induced for carrier protein expression with IPTG and four hours later pldA expression was induced (DOX at concentrations indicated) and cultures were incubated for 16 hours. 2 OD of culture was subjected to periplasmic isolation (Epicentre Technologies, an Illumina Company, Madison, WI) while 1.5 ml was brought to 150 mM Tris pH 7.75, 5 mM EDTA and extracted for 24 hours at 25° C. with shaking. Extracted values are from medium supernatant after extraction and centrifugation.
Figure 5B:
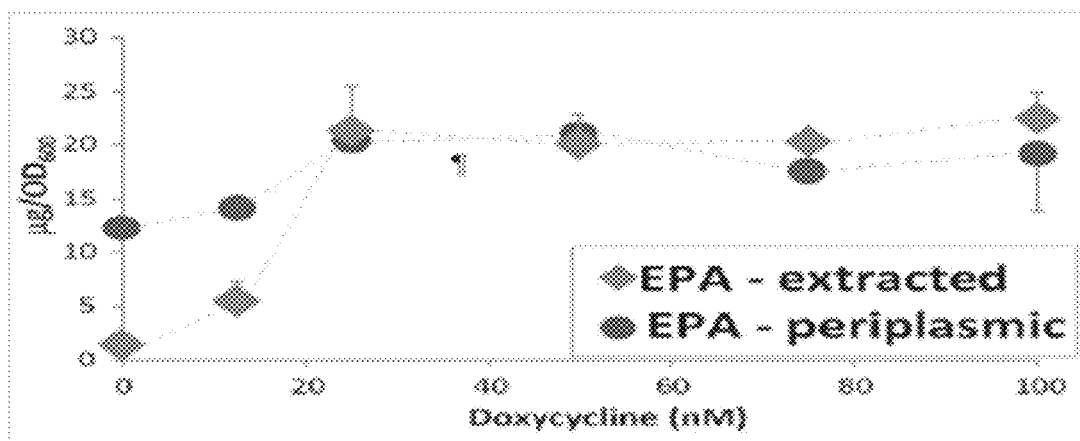
Figure 5C:
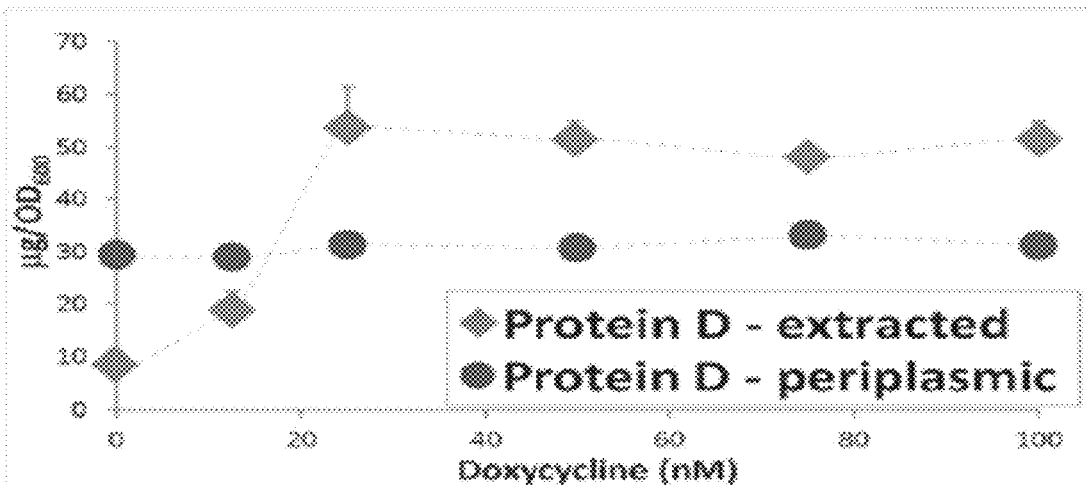

Next, a series of enzymes were examined that the inventors predicted might facilitate more complete extraction from the periplasm using shake-flask culture. An E. coli outer membrane phospholipase A (OmpLA) enzyme (encoded by the gene pldA) was found to enhance the extraction of all three carrier proteins in shake-flask culture. (FIGS. 5A-C). Several other E. coli phospholipases were also tested. GlpQ, PldB and TesA were also found to enhance the extraction of carrier proteins, although to a lesser extent than OmpLA.

In these shake-flask culture experiments, each expression plasmid was modified such that the plda gene was positioned downstream of each carrier protein (bicistronic construct) and placed under separate control (i.e., each carrier protein was induced by IPTG and pldA expression was induced by doxycycline (DOX)). The plasmid was then sequence verified and subcloned into MDS69meta (aka SG69meta aka T69meta). To establish robust carrier protein expression levels, pldA expression was induced four hours following induction of the recombinant carrier protein. Results after 16 hours of extraction for each carrier protein are shown in FIGS. 5A-C. In each case, the amount of carrier protein extracted equaled or exceeded the amount present in the periplasm based on the Epicentre protocol. Higher levels of Protein D were present in the medium post-extraction compared to the periplasm because moderate levels of Protein D "leaked" from the cells during culturing consistent with the experiments described above. Very little DOX was required to achieve OmpLA levels that resulted in complete extraction of each carrier protein, an important feature for commercialization scale-up.

Production of the three recombinant carrier proteins (Exoprotein A (rEPA), Protein D (PD) and CRM197) in the periplasm and secretion into the medium was investigated in shake-flask culture with reduced genome E. coli host strain MDS69meta recA (aka T69meta recA or SG69meta recA) which comprises the deletions made to create MDS69meta (described above) and also comprises a deletion of recA, using several expression strategies.

The host cells in each case were transfected with a single expression plasmid construct comprising a sequence encoding EPA, PD or CRM197 fused to a YtfQ secretion signal under the control of an IPTG-inducible promoter and further comprising a sequence encoding OmplA under the control of a doxycycline (DOX) inducible promoter.

Stock cultures of the host cells stored at −80° C. were thawed and used to inoculate 10 mL of defined medium (Korz media supplemented with 0.2% glucose and 50 µg/ml kanamycin). Precultures grew overnight and were used to inoculate shake flasks at equal initial cell densities. Once the cells reached saturation, the target gene (EPA, PD or CRM197) was induced with 50 µM IPTG (EPA and CRM 197) or 100 µM IPTG (PD) (very late induction) and pldA expression was induced ~4 hours later with 0 to 100 nM DOX and the induction was allowed to continue overnight at 25° C. The growth rates and final cell densities were comparable among the strains.

The following morning, 1335 µl of culture was collected and placed in several 2 ml tubes containing concentrated Tris and EDTA (final conditions=1.5 ml, 150 mM Tris pH 7.75, 5 mM EDTA). The tubes were then incubated for 2 hours (shaking at 25° C.) prior to assessing yield or 2 hours (shaking at 25° C.) followed by incubation overnight (at 25° C.) prior to assessing yield. For PD, tubes were also incubated for 2 hours (shaking at 25° C.) followed by a 6 hour incubation at 25° C.

After 2 hours, 6 hours, or overnight shaking, the tubes were centrifuged at 4000×g for 15 minutes, 500 µl of supernatant was removed and applied to a YM10 spin filter and centrifuged at 13000×g for 30 minutes. The retentate (representing media) was diluted to the equivalent of 0.02 OD/µl with Korz/0.2% glucose/Kan (25 µg/ml)/Tris-EDTA. To assess periplasm yield, an epicentre Peri-Prep was performed on a separate aliquot of culture, final concentration=0.2 OD/µl. All samples were analyzed on a Caliper chip.

Figure 7:
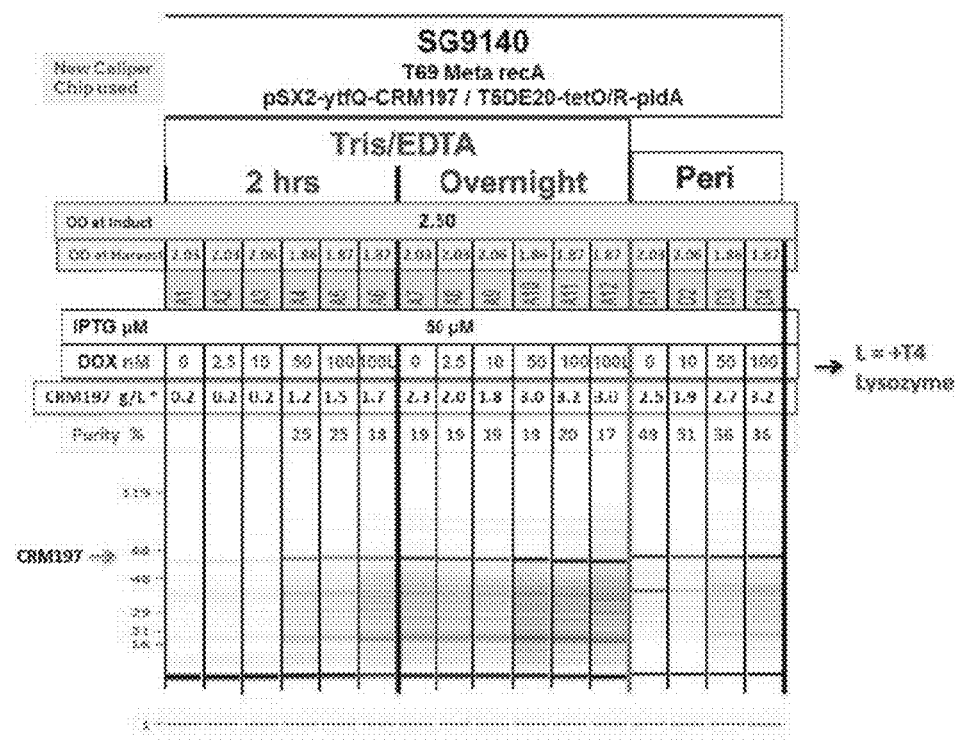
Figure 8:
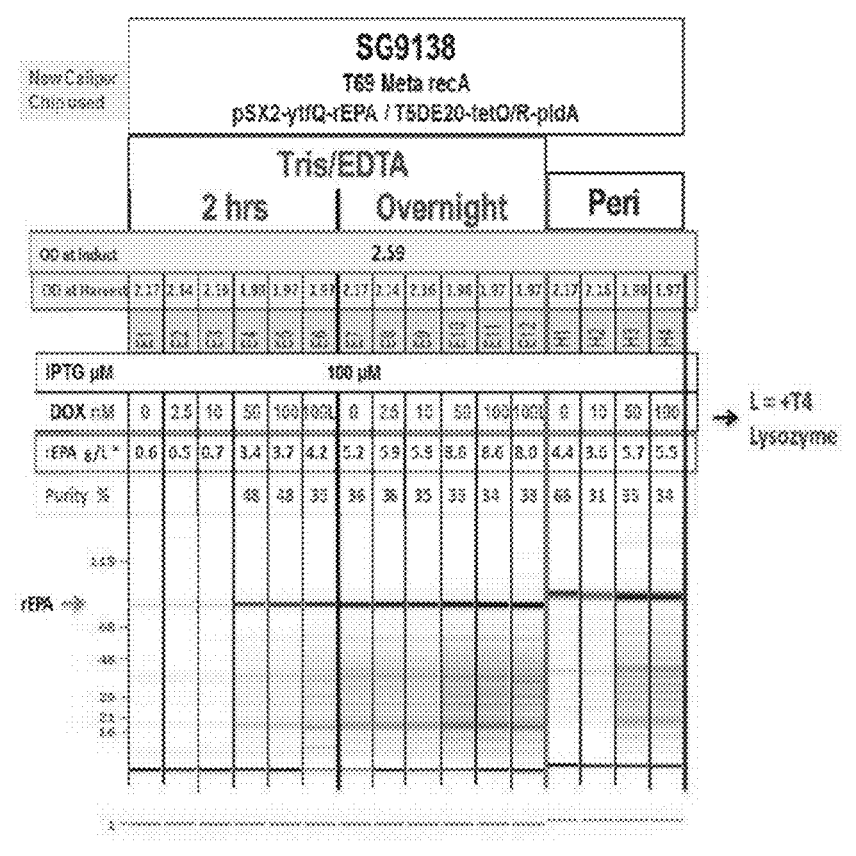
Figure 9:
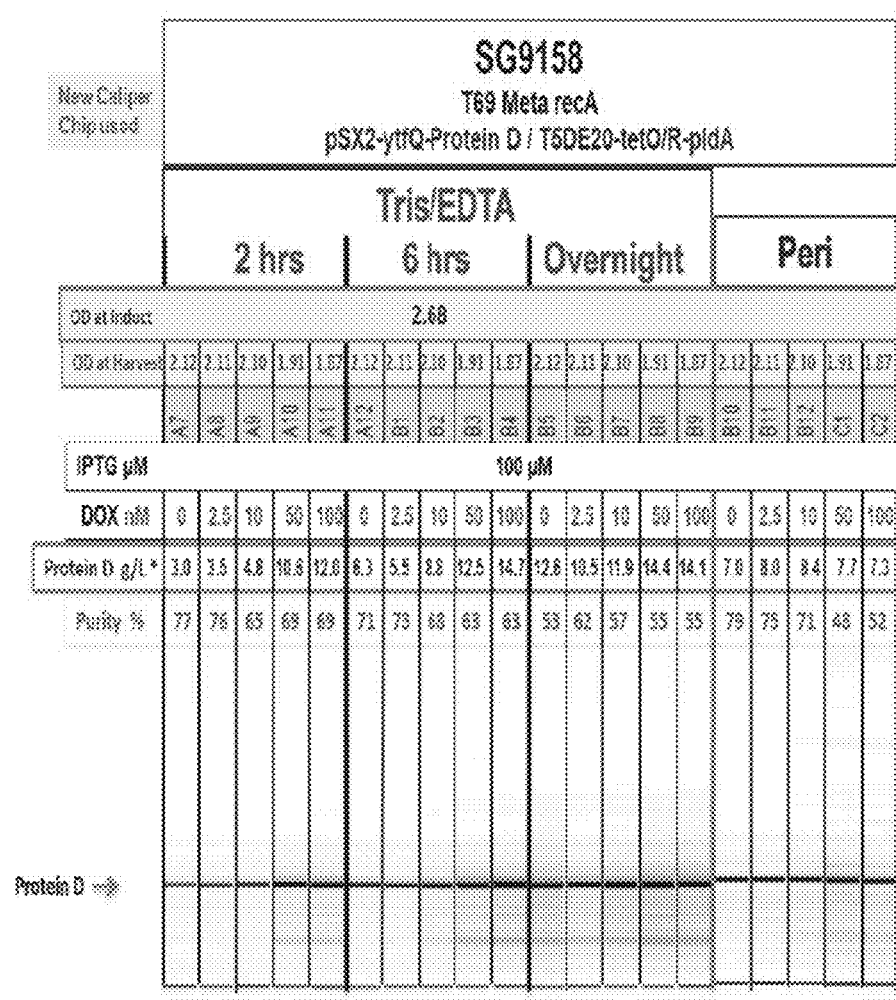
FIG. 9 illustrates the effect of co-expression of a phospholipase (OmpLA is exemplified) on release of recombinant Protein D (PD) into the medium in reduced genome E. coli strain T69 Meta recA (aka MDS69meta recA) carrying a single plasmid expression vector encoding PD fused to a YtfQ secretion signal (under the control of an IPTG-inducible promoter) and encoding OmpLA under the control of a doxycycline-inducible promoter. PD and OmpLA were induced once host cells reached saturation in shake flask culture and yield of soluble PD in the medium and periplasm was assessed following a 2 hour, 6 hour or overnight incubation with Tris/EDTA.

As can be seen from FIGS. 7-9, co-expression of the pldA gene resulted in extraction of nearly 100% of each of the carrier proteins into the media confirming that the method is not limited to any particular recombinant protein. Overnight extraction with Tris/EDTA released substantially more target protein than the 2 hour extraction, with nearly all of the protein extracted to the medium during the 6 hour and overnight extractions (compare periplasm yield to extracted yield—if they are the same then all of the protein has been extracted).

Figure 10A:
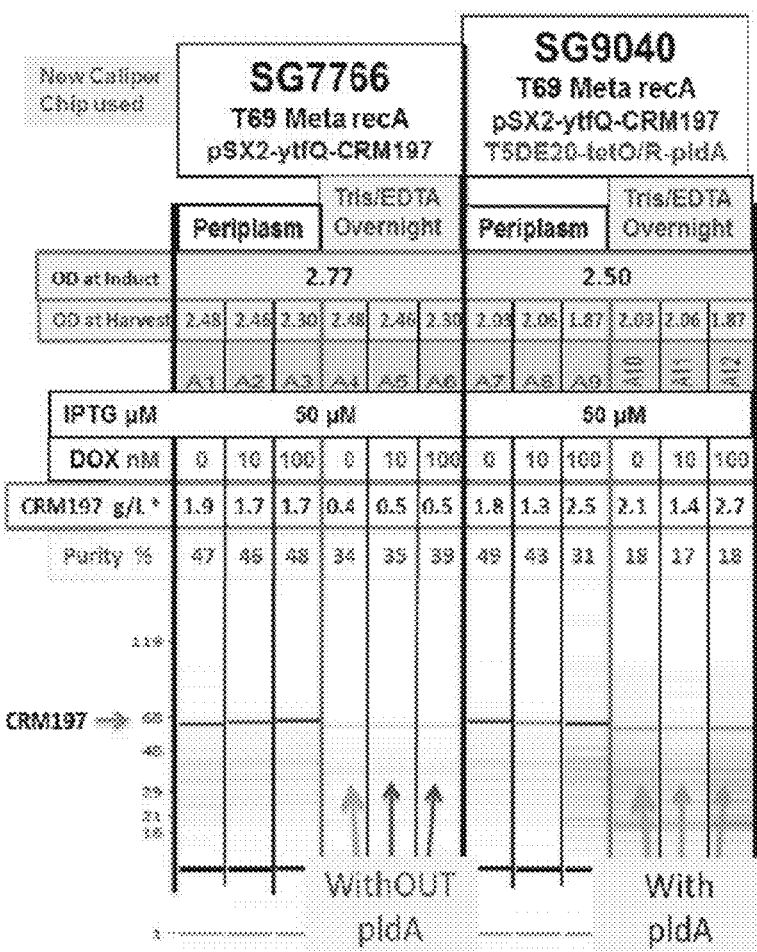
FIGS. 10A-C illustrate basal endogenous (SG7766 $2^{nd}$ 0-100 nm DOX-left panel in 10A lanes 4-6) and basal endogenous+uninduced (SG9040 lane 4) OmpLA levels (as measured by release of carrier protein into the medium in the absence of DOX) in strain T69 Meta recA (aka MDS69meta recA) carrying a single plasmid expression vector encoding either CRM197 (FIG. 10A), Protein D (FIG. 10B) or rEPA (FIG. 10C) fused to a YtfQ secretion signal (under the control of an IPTG-inducible promoter) and encoding OmpLA under the control of a single Tetracycline Operator (tetO) doxycycline-inducible promoter by comparison to the same T69 Meta recA (aka MDS69meta recA) strain carrying a single plasmid expression vector encoding only CRM197 (FIG. 10A), Protein D (FIG. 10B) or rEPA (FIG. 10C) fused to a YtfQ secretion signal under the control of an IPTG-inducible promoter (i.e. sequence encoding OmpLA is absent from this vector). Co-expression of the phospholipase significantly increased release of carrier protein in the medium—about 5-fold for rEPA and CRM197 at the highest inducer concentration and ~3-fold for PD at the highest inducer concentration.
Figure 10B:
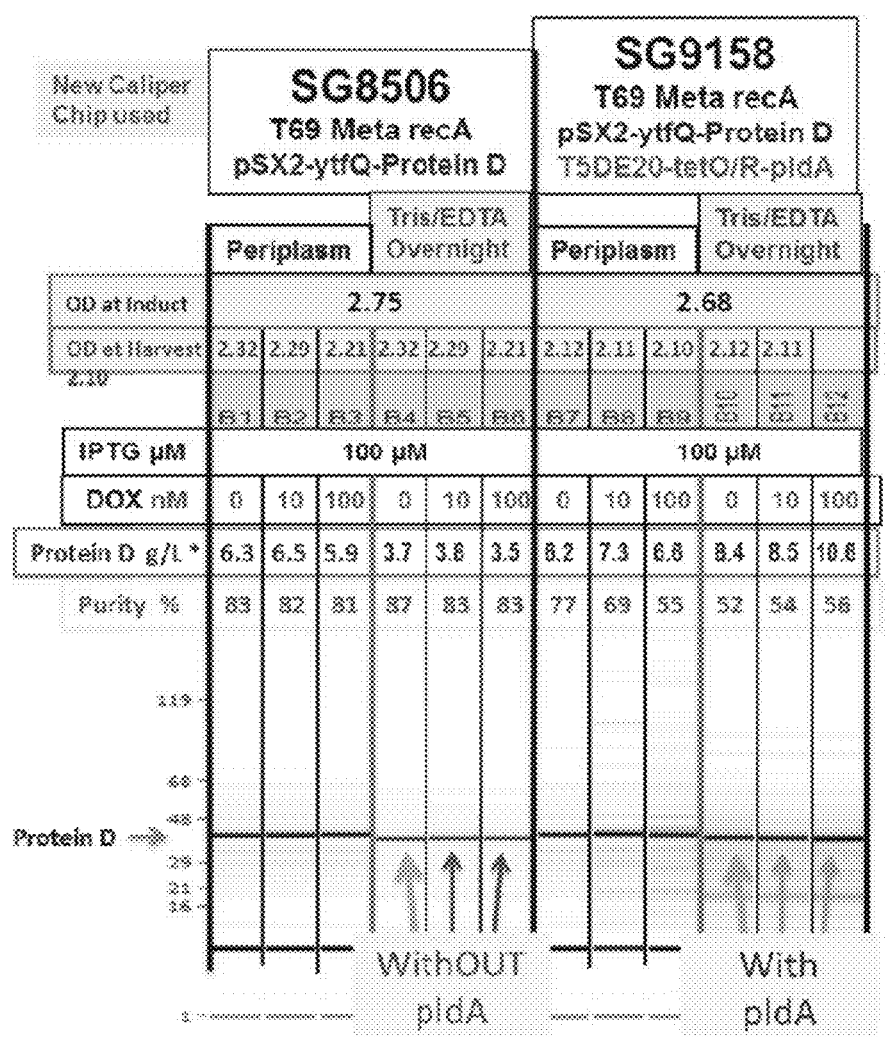
Figure 10C:
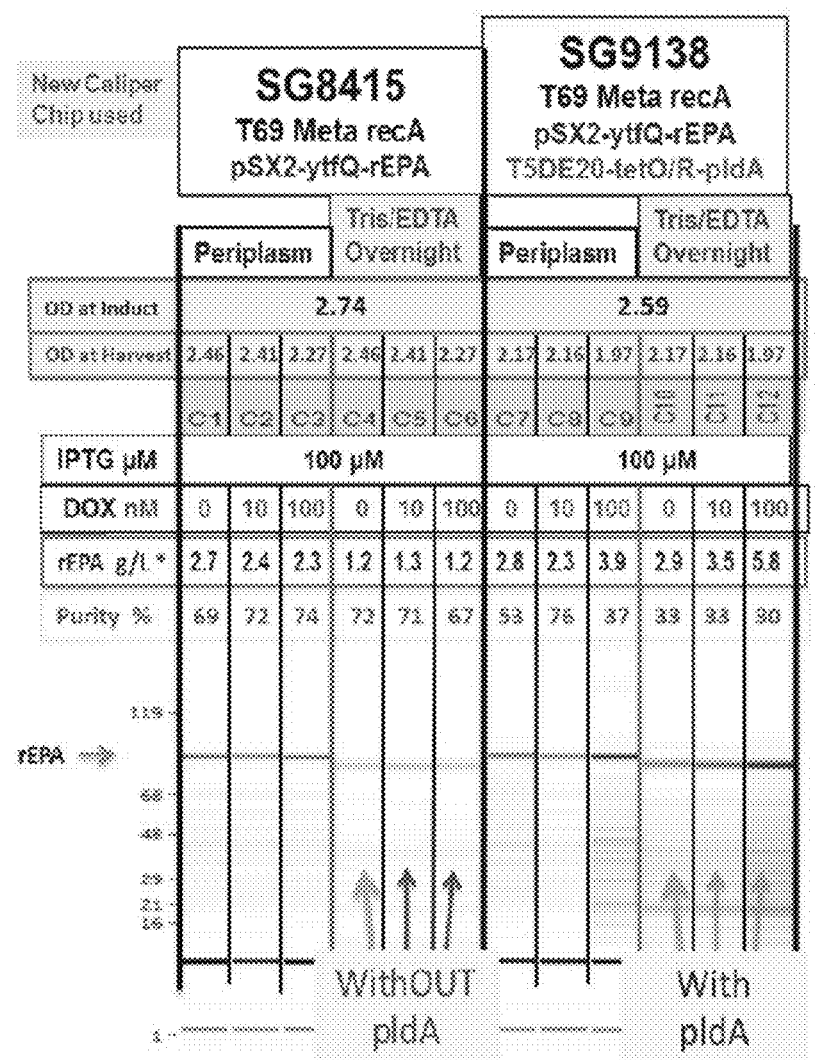

One curious observation was the fact that some of the carrier protein was released at these prolonged extraction times even in cultures in which expression of pldA was not induced (0 DOX). The promoter controlling pldA expression is known to have some un-uninduced basal activity based on prior experiments with GFP. Therefore, it was assumed that pldA expression levels are likely higher than wildtype in a strain carrying a pldA based plasmid. To test that assumption, Tris/EDTA extraction of targets from MDS69meta recA strain transformed with expression vector encoding only the recombinant carrier proteins were compared with expression vector encoding recombinant carrier proteins and OmpLA. All strains were induced for the target with IPTG and then treated with 0, 10 or 100 nM DOX and subsequently subjected to an overnight extraction in Tris/EDTA extraction buffer. The results demonstrate that even in the absence of induction of pldA expression, significantly more target is extracted from a strain carrying the pldA based plasmid, indicating leaky basal expression of OmpLA in the un-induced state. See FIGS. 10A-C. 2-3 g/L yield of CRM197 in the media was obtainable using this procedure.

Because leaky expression of OmpLA was observed with a single tet operator (as in the carrier protein experiments above), pldA was placed under the control of dual tet operators in the following experiments. MDS69meta recA host cells were transfected with a single expression plasmid construct comprising a sequence encoding EPA, PD or CRM197 fused to a YtfQ secretion signal under the control of an IPTG-inducible promoter and further comprising a sequence encoding OmpLA controlled by dual tet-operators.

Stock cultures of the host cells stored at −80° C. were thawed and used to inoculate 10 mL of defined medium (Korz/0.2% glucose/kanamycin (25 μg/ml)). Precultures grew overnight and were used to inoculate shake flasks at equal initial cell densities. Once the cells reached saturation, the target gene (EPA, PD or CRM197) was induced with 100 μM IPTG (EPA and CRM 197) or 200 μM IPTG (PD) (very late induction) and pldA expression was induced ~4 hours later with 0, 12.5, 25, 50, 75 or 100 nM DOX and the induction was allowed to continue overnight at 25° C. The growth rates and final cell densities were comparable among the strains.

The following morning, 1335 μl of culture was collected and placed in several 1.5 ml tubes containing concentrated Tris and EDTA (final conditions=1.5 ml, 150 mM Tris pH 7.75, 5 mM EDTA). The tubes were then incubated for 6 hours (shaking at 25° C.) or overnight prior to assessing yield.

After 6 hours or overnight shaking, the tubes were centrifuged at 4000×g for 15 minutes, 500 μl of supernatant was removed and applied to a YM10 spin filter and centrifuged at 13000×g for 30 minutes. The retentate (representing media) was diluted to the equivalent of 0.02 OD/μl with Korz/0.2% glucose/Kan (25 μg/ml)/Tris-EDTA. To assess periplasmic yield, an Epicentre Peri-Prep was performed on a separate aliquot of culture, final concentration=0.2 OD/μl. All samples were analyzed on a Caliper chip.

Figure 11:
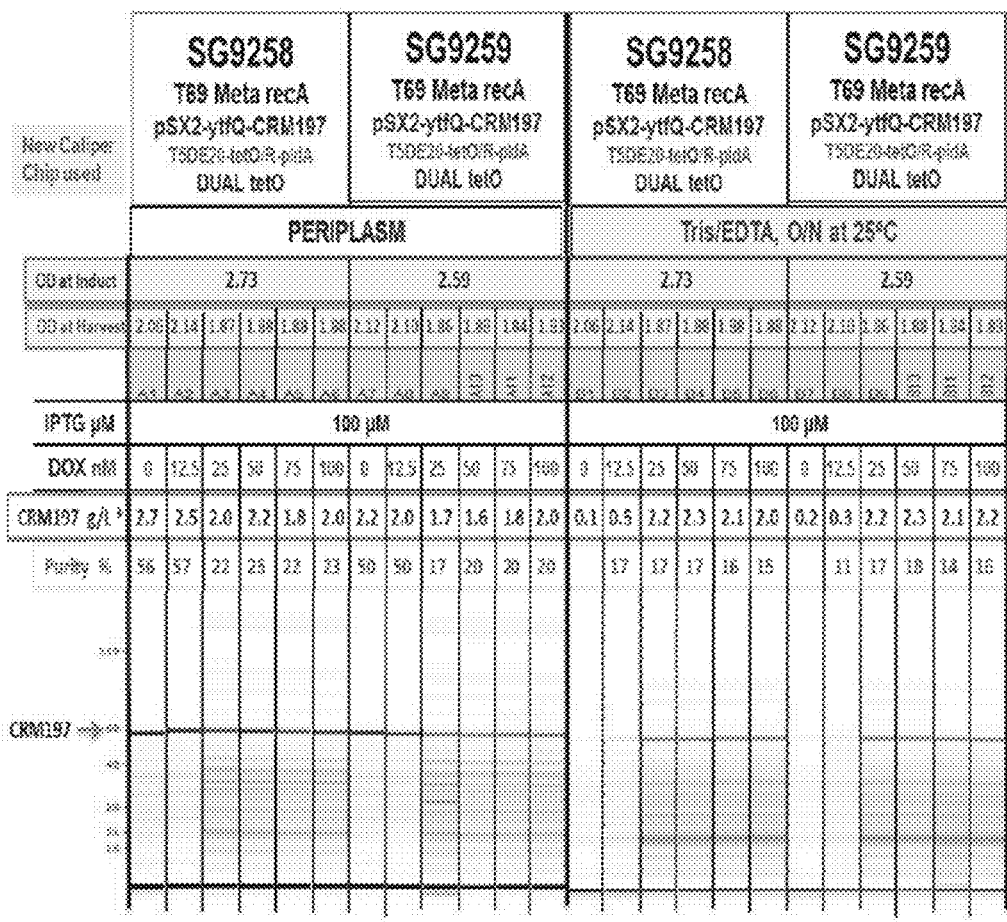
FIG. 11 illustrates yield of CRM197 in the periplasm and Tris/EDTA extraction at 25° C. following induction of expression of CRM197 and OmpLA in T69 Meta recA (aka MDS69meta recA) host cells carrying a single expression plasmid comprising sequence encoding CRM197 under the control of an IPTG-inducible promoter and pldA under the control of a doxycycline-inducible promoter comprising dual tet operators. Very little CRM197 appears in the Tris/EDTA extraction at 25° C. in the absence of DOX, but increases significantly when pldA is induced. Periplasmic yield of CRM197 is not affected by pldA gene expression.

Data for CRM197 is shown at FIG. 11. Very little CRM197 is released by Tris/EDTA extraction unless DOX is added to induce expression of the pldA gene. This is in stark contrast to previous results obtained with single-tetO constructs (as above, FIG. 10A). In those cases, typically 50% or more of the carrier protein was released after overnight Tris/EDTA extraction in the absence of induction of pldA gene expression by DOX due to un-induced basal expression of pldA. Similar results were observed for PD and EPA (data not shown). Thus, Tris/EDTA extraction of carrier protein in the absence of induced pldA expression is observed only when expression of pldA is controlled by a leaky (e.g. single tetO) promoter and is due to uninduced background OmpLA.

As previously seen, due to PD's inherent lipase activity, more PD is released in the absence of DOX (which induces OmpLA) relative to CRM197 and EPA and this is also true for the dual tetO-pldA construct. However, when using the dual tetO-pldA construct, only $\frac{1}{8}^{th}$ of the PD is released in the absence of induction of pldA expression compared to ½ or more with the single tetO-pldA construct (data not shown).

Minimizing expression of the target carrier protein and OmpLA in the un-induced state is favorable for continuous fermentation to avoid potential selection bias.

The single plasmid/two-promoter constructs described above gave 2-3 g/L yields of CRM197 in the media; however, these constructs were found to tend to form plasmid dimers. Therefore, a bicistronic message approach was tested in which an RBS (ribosome binding site) pldA insert was placed immediately downstream of CRM197 under the control of a DOX-inducible promoter. In this construct, expression of both CRM197 and OmpLA are induced by DOX. Employing this construct in the procedure described above yielded 4-5 g/L based on periplasm preps and 4 g/L based on Tris/EDTA extracts (data not shown).

In some experiments, the bicistronic CRM197-RBS pldA construct was modified to replace the wildtype pldA with a codon-altered pldA to greatly decrease the chance of chromosomal integration. At the same time, three different RBS sequences were tested to determine if co-expression of CRM197 and OmpLA can be optimized to improve yield of CRM197.

Example 4

Optimizing CRM197 Inducer Concentration and Extended Analysis of CRM197 Release to the Medium in MDS69meta T/A LowMut recA Cells In previous experiments, the medium sample to monitor release of CRM197 was taken after the overnight induction period. A better control sample would be generated by taking the medium sample from an aliquot of overnight induced culture that was then incubated in parallel with the Tris/EDTA extraction samples (incubated overnight again at 25° C. with shaking).

Previous experiments indicated that optimal CRM197 expression was achieved over a range of doxycycline concentrations of 50-250 nM but began to decline at 500 nm and above.

The following experiment tested induction with 100, 250 and 400 nM DOX and analyzed the release of CRM197 to the medium using improved controls.

Figure 6A:
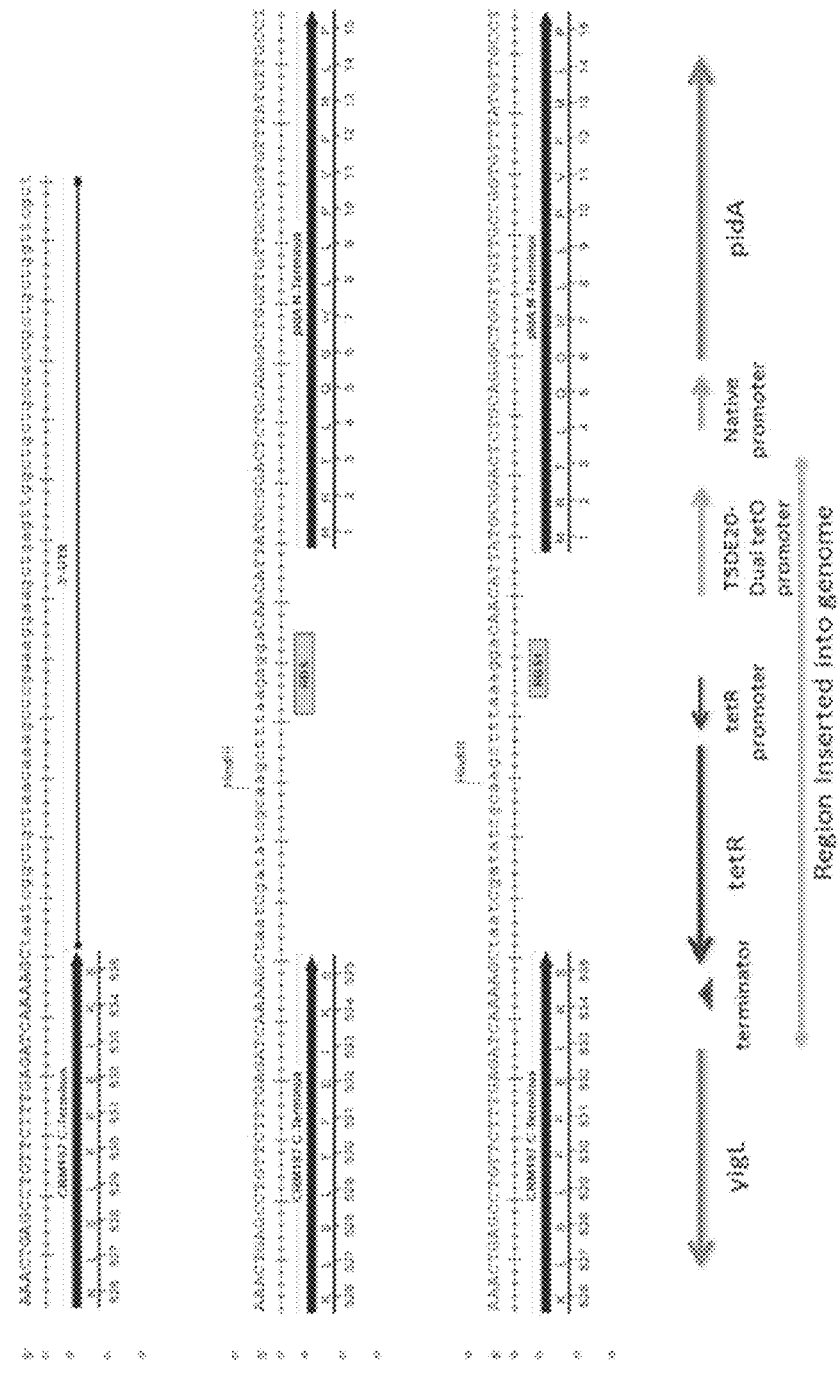
Figure 6B:
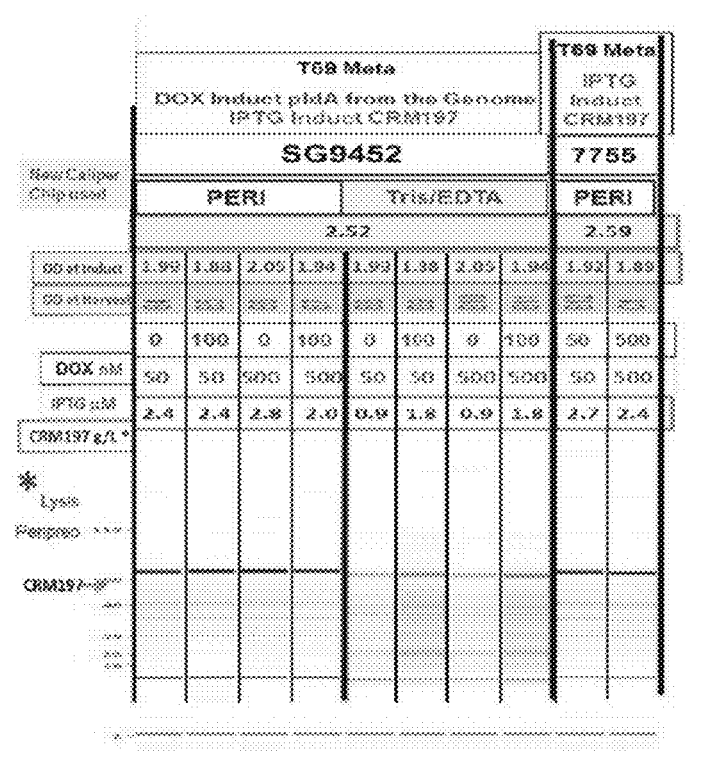

Briefly, MDS69meta T/AT LowMut recA host cells carrying expression plasmid encoding (i) CRM197 fused to a YtfQ secretion signal under the control of a doxycycline promoter or (ii) CRM197 fused to a YtfQ secretion signal and codon optimized pldA sequence under the control of the same doxycycline promoter (2 separate constructs were employed differing only with respect to the RBS between CRM197 and the pldA ORFS, see FIG. 6A), were induced (very late induction) with 100, 250 or 400 nM DOX (medium=Korz/0.2% Glucose/Kan). To assess periplasmic yield, an Epicentre Peri-Prep was performed on an aliquot of culture equivalent to 2 ODs, final concentration of prep equivalent to 2 OD/µl. To determine yield of CRM197 in the media, 1335 µl of induced culture was placed in a 1.5 ml tube containing concentrated Tris and EDTA (final conditions=1.5 ml, 150 mM Tris, pH 7.75, 5 mM EDTA) and all samples were subjected to shaking overnight at 25° C. Supernatant was harvested by cfg at 4000×g for 15 minutes. 500 µl of supernatant was removed and applied to a YM10 spin filter and cfg at 13000×g for 30 minutes. The retentate was diluted to the equivalent of 0.02 OD/µl with Korz/0.2% Glucose/Kan (25 µg/ml)/Tris-EDTA.

Medium control 1: One ml of the induced culture was placed in a 1.5 ml tube and subjected to overnight shaking at 25° C. alongside the Tris/EDTA extraction.

Medium control 2: One ml of the induced culture was placed in a 1.5 ml tube and stored at 4° C. for 2 days.

Supernatants from both medium samples were harvested and processed according to the same procedure as the Tris/EDTA extract. Final dilution to 0.02 OD/µl was performed with Korz/0.2% Glucose/Kan (25 µg/ml)/Tris-EDTA.

Figure 12A:
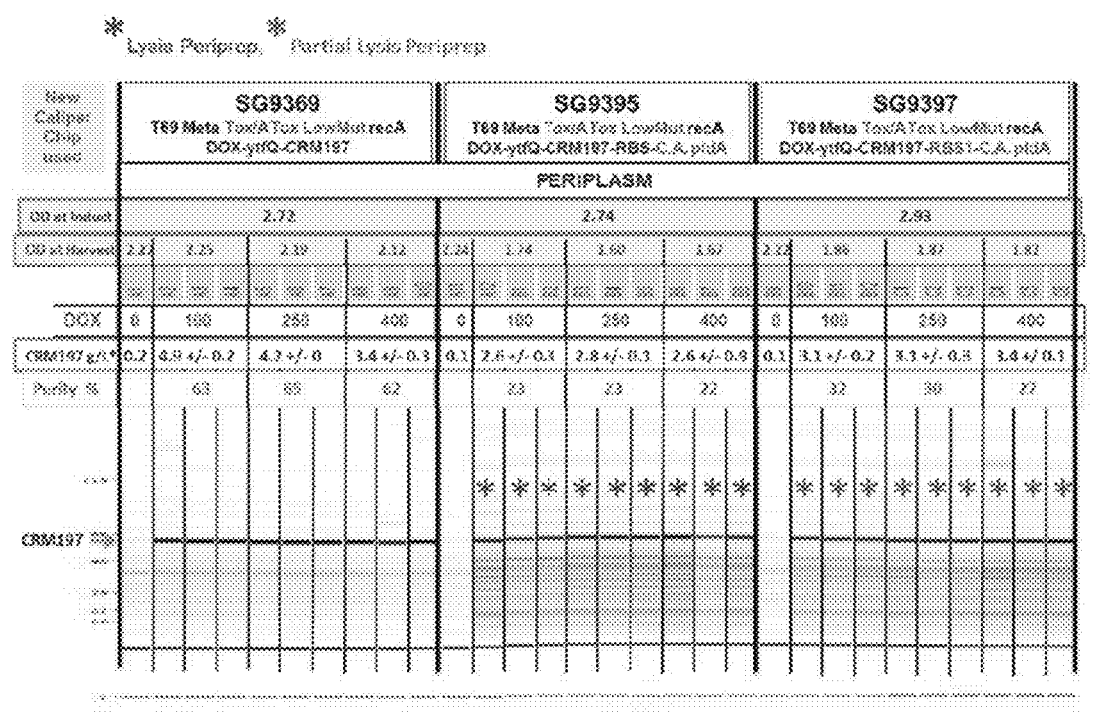

The maximum concentration of DOX to use for the optimal induction of YtfQ-CRM197 from these strains is 400 nM (see FIG. 12C).

Figure 12B:
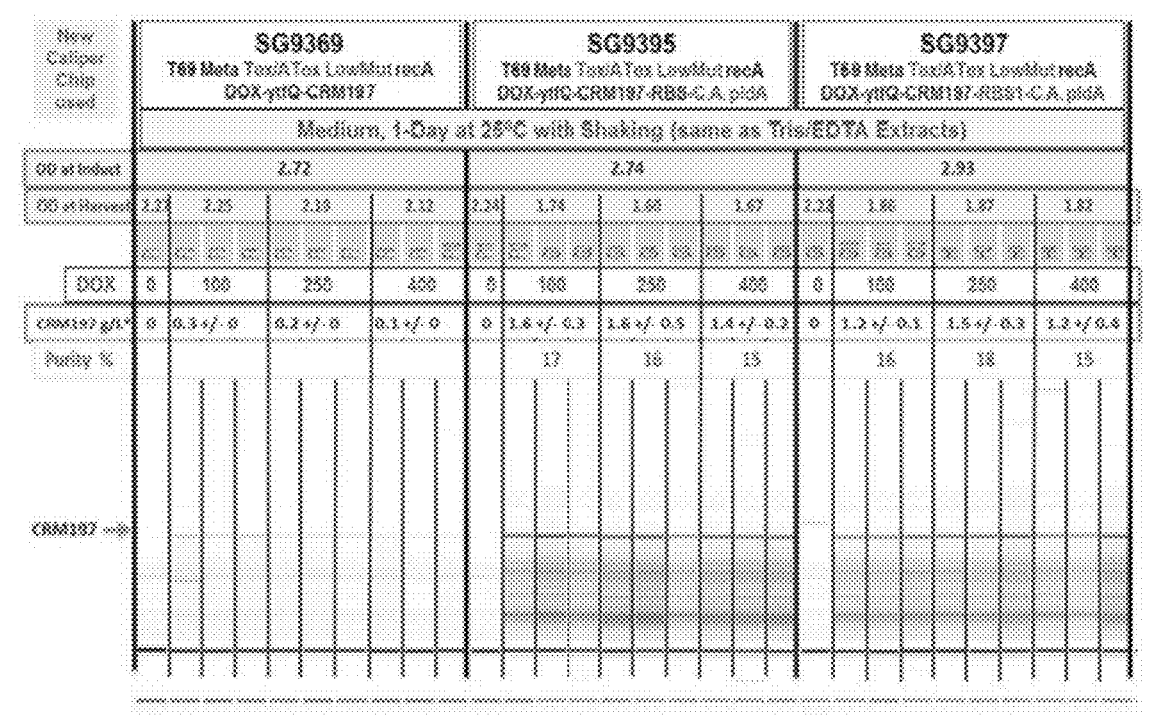
Figure 12D:
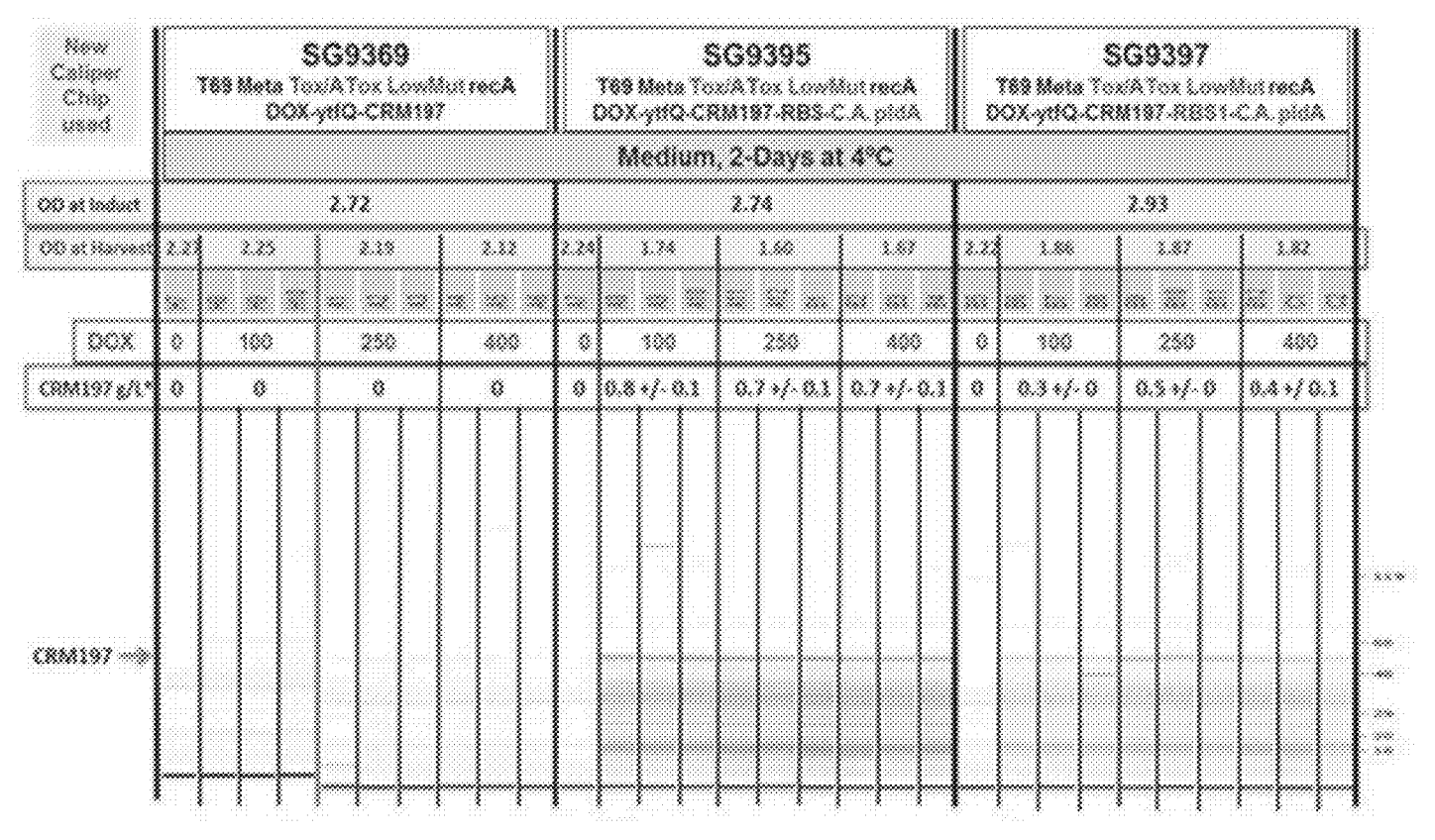

Storage of induced cultures at 4° C. led to significantly less release of CRM197 to the medium than incubating at 25° C. with shaking (compare FIGS. 12B and 12D). Approximately 50% of the CRM197 expressed in OmpLA-coexpressing strains can be released simply by incubating at 25° C. with shaking in the absence of extraction buffer (FIG. 12B). With extraction buffer, nearly 100% of the CRM197 can be released.

These data demonstrate that, although a wide variety of configurations can be used to co-express a phospholipase and protein of interest according to the methods described herein with very good results, optimal results in terms of both expression of the protein of interest and extraction of the protein of interest into the medium were achieved using bicistronic construct encoding the protein of interest and the phospholipase separated by an RBS (and under the control of the same promoter, in this case a DOX-inducible promoter), with virtually 100% of the protein of interest extracted into the medium. Moreover, the strength of the ribosome binding site (RBS) was found to directly correlate with the amount of OmpLA expressed (see right two panels of FIG. 12A demonstrating that the pldA gene is expressed at different levels due to the differences in strength of the RBS).

Example 5

CRM197 Periplasmic Yield in Wild Type E. coli Strains and E. coli Strains with RNase III+Toxin/Antitoxin Gene Deletions The periplasmic yield of CRM197 was measured in several E. coli strains including strain MG1655 (the native parent strain of the multiple deletion strain E. coli herein described), wild type K12 strain W3110 and BL21DE3 strain (with and without phage deletions) using OmpF or YtfQ secretion signals to direct CRM197 to the periplasm.

Figure 13:
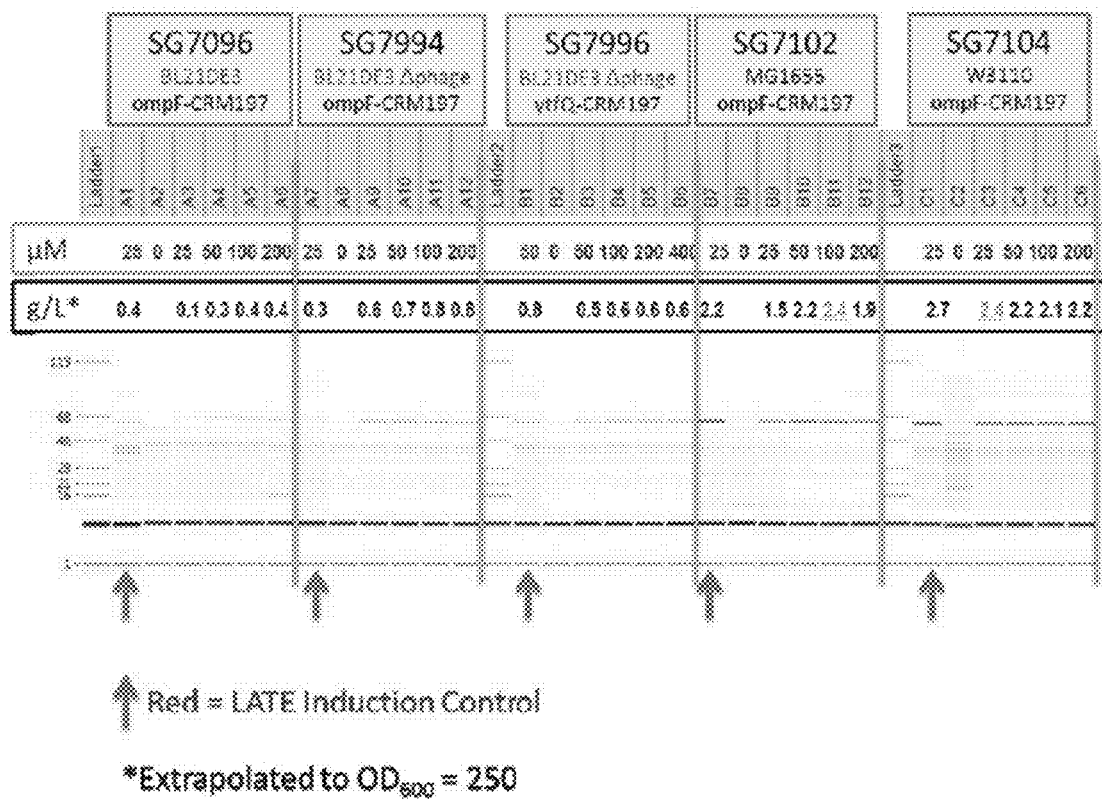
FIG. 13 illustrates a comparison of periplasmic production of CRM197 from several E. coli strains.
Figure 14:
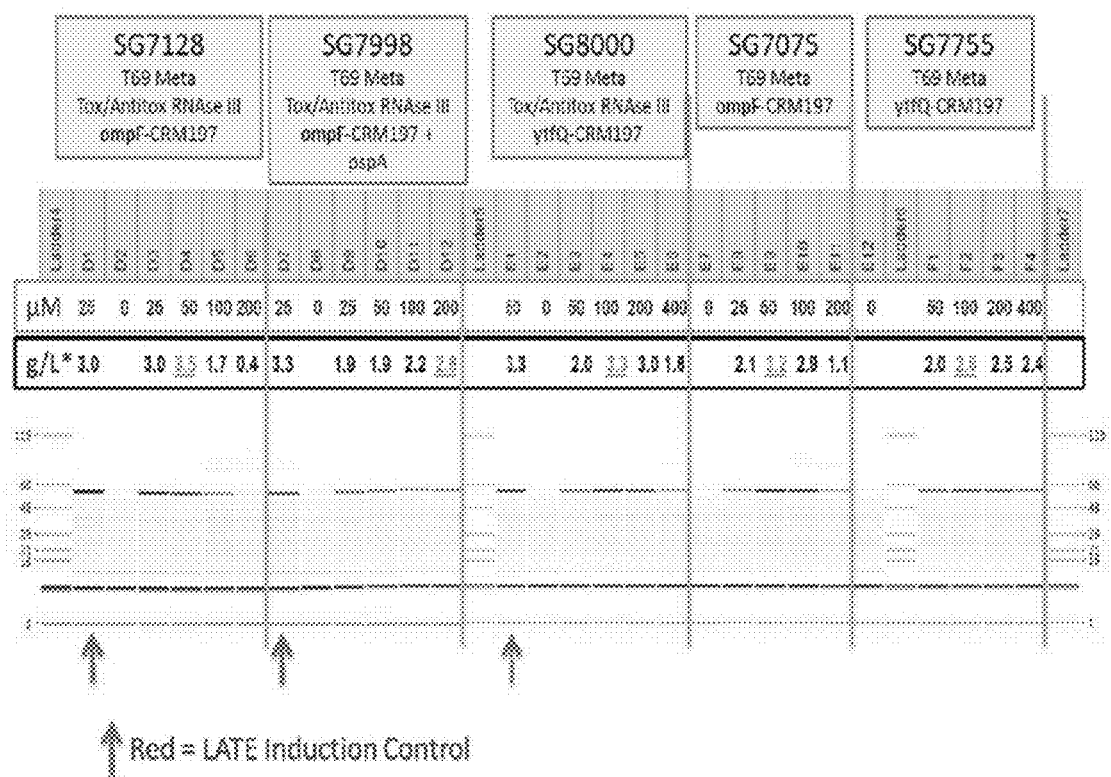
FIG. 14 illustrates periplasmic yield of CRM197 in a strain from which RNase III and toxin/antitoxin genes were deleted compared to parent strains comprising these genes.

FIG. 13 demonstrates periplasmic production of CRM197 in the following strains: (1) BL21DE3 (2) BL21DE3 with phage deletions (3) MG1655 and (4) W3110. Briefly, each strain carrying the expression plasmid was grown at 25° C. until the OD600 was sufficient for late induction (0.3 OD600) or very late induction (1.5-2.0 OD600). For late induction, a 20 ml aliquot of culture was removed to a 125 ml baffled Erlenmeyer flask and induced with 25 µM IPTG for OmpF-CRM197 constructs and 50 µM IPTG for YtfQ-CRM197 constructs. For very late induction, a 20 ml aliquot of culture was removed to a 125 ml baffled Erlenmeyer flask and induced with 25-200 µM IPTG for ompF-CRM197 constructs and 500-400 μM IPTG for YtfQ-CRM197 constructs. All inductions were grown at 25° C. for 20 hours, after which 2 ODs of culture were harvested and periplasmic and spheroplast fractions were prepared using Epicentre Periplasting method.

Expression of CRM197 in the *E. coli* B strain BL21DE3 was significantly improved by deleting phage. Similar results were obtained whether OmpF or YtfQ secretion signals were employed.

The periplasmic yield of CRM197 was assessed in reduced genome *E. coli* strains designed to increase the amount of mRNA transcript by (i) deleting toxin-antitoxin genes that target RNA and (ii) deleting RNAse III. CRM197 production in strain T69meta Tox/Antitox RNase III (comprising the deletions of MDS69, a partial (inactivating) deletion of RNase III, and deletion of toxin-antitoxin genes that target RNA) was compared to CRM197 production in strain T69meta.

As illustrated in FIG. 14, combined deletion of RNA-targeting toxin/antitoxin genes and RNase III significantly increased the periplasmic yield of CRM197 regardless of whether OmpF or YtfQ signal sequence was used to direct CRM197 to the periplasm (yield of 3.5 and 3.3 g/L in strains SG7128 and SG800 compared to 2.6 g/L in strain SG7755). Additive and even synergistic increases in the yield of recombinant proteins may be obtainable in *E. coli* strains comprising deletion of toxin-antitoxin genes and RNase III. Co-expression of the chaperone pspA did not increase the yield of CRM197 and even tended to lower the yield, probably due to diversion of the cell machinery to producing the chaperone.

The results are summarized at Table 2 below:

TABLE 2

CRM197 Periplasm Expression Results 25° C.

| Strain | LATE Induction Control Result | VERY LATE Induction Result |
|---|---|---|
| SG7096 (ompF-CRM) BL21(DE3) | Very Weak Expression at 25 μM | Very Weak Expression at 50-200 μM |
| SG7994 (ompF-CRM) BL21(DE3) Δphage | Very Weak Expression at 25 μM | Weak Expression at 25-200 μM |

TABLE 2-continued

CRM197 Periplasm Expression Results 25° C.

| Strain | LATE Induction Control Result | VERY LATE Induction Result |
|---|---|---|
| SG7996 (ytfQ-CRM) BL21(DE3) Δphage | Weak Expression at 50 μM | Weak Expression at 50-400 μM |
| SG7102 (ompF-CRM) MG1655 | Good Expression at 25 μM | Good Expression at 50-100 μM |
| SG7104 (ompF-CRM) W3110 | Good Expression at 25 μM | Good Expression at 25-200 μM |
| SG7990 (MDS42 Meta Low Mut msbB ecA recA + pSX2-ytfQ CRM197) | Good Expression at 50 μM | Good Expression at 50-100 μM |
| SG7128 (T69 Meta Tox/Antitox Interm. RNAse III + pSX2-ompF CRM197) | Strong Expression at 25 μM | Strong Expression at 25-50 μM |
| SG7998 (T69 Meta Tox/Antitox Interm RNAse III + pSX2-ompF CRM197 + pspA) | Strong Expression at 25 μM | Good Expression at 100-200 μM |
| SG8000 (T69 Meta Tox/Antitox Interm. RNAse III + pSX2-ytfQ CRM197) | Strong Expression at 50 μM | Strong Expression at 100-200 μM |
| SG7075 (ompF-CRM197) T69 Meta | Not Done | Strong Expression at 50 μM (repeat load from previous expt) |
| SG7755 (ytfQ-CRM197) T69 Meta | | Good/Strong Expression at 100-400 μM (repeat load from previous expt) |

Example 6

Figure 15:
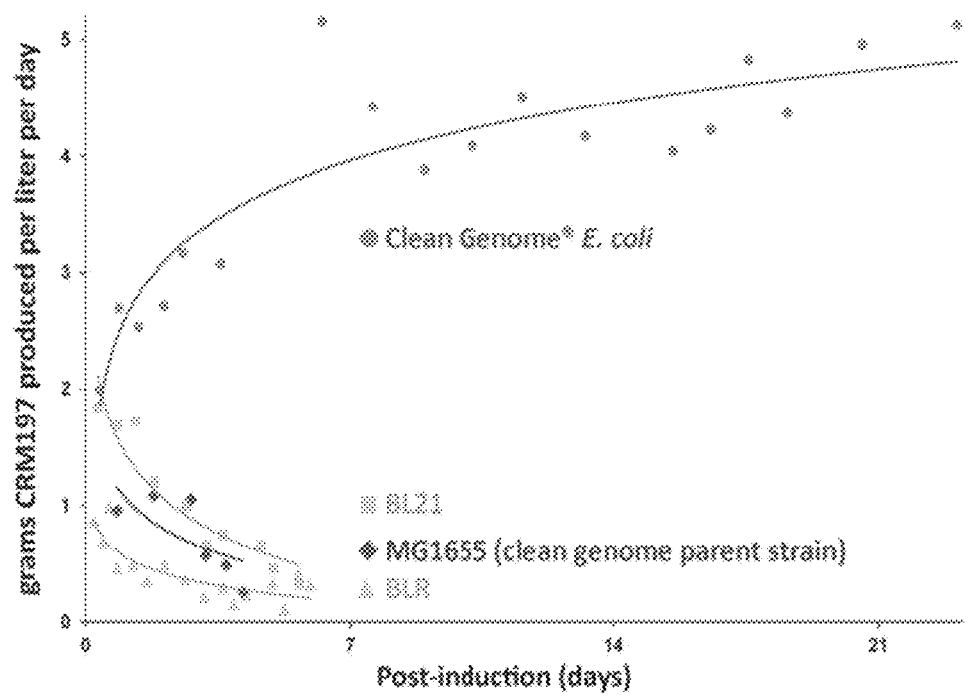
FIG. 15 illustrates production of CRM197 during long term continuous culture of a reduced genome E. coli strain (SG69 meta aka MDS69meta) carrying an expression vector encoding CRM197 fused to a periplasmic expression signal sequence compared to production of CRM197 in commonly used fermentation hosts carrying the same expression plasmid. A fermentation producing between 4 and 6 grams of CRM197 per liter per day is shown. Data points are Wes capillary electrophoresis chemiluminescent immunoassay signals converted to CRM197 expression values using a CRM197 standard curve. Recognition of CRM197 was with anti-CRM197 polyclonal antisera and HRP-luciferase chemiluminescence

Continuous Fermentation System for Production of Carrier Proteins and Extraction into the Media Reduced genome *E. coli* strains can sustain continuous growth and protein production for over 60 days in continuous fermentation culture (continuous flow or "C-Flow"). See FIG. 15, illustrating continuous growth and production of CRM197 at a (periplasmic) yield of 4-5 g/liter/day over a period of over 30 days (three weeks are shown), which is not possible with conventional *E. coli* production strains BL21, MG1655 and BLR in which yields of ~1 g/L are obtained initially (which steadily decreases) and in which continuous fermentation cannot be sustained for periods longer than a few days as non-producing mutants take over the culture.

Figure 16:
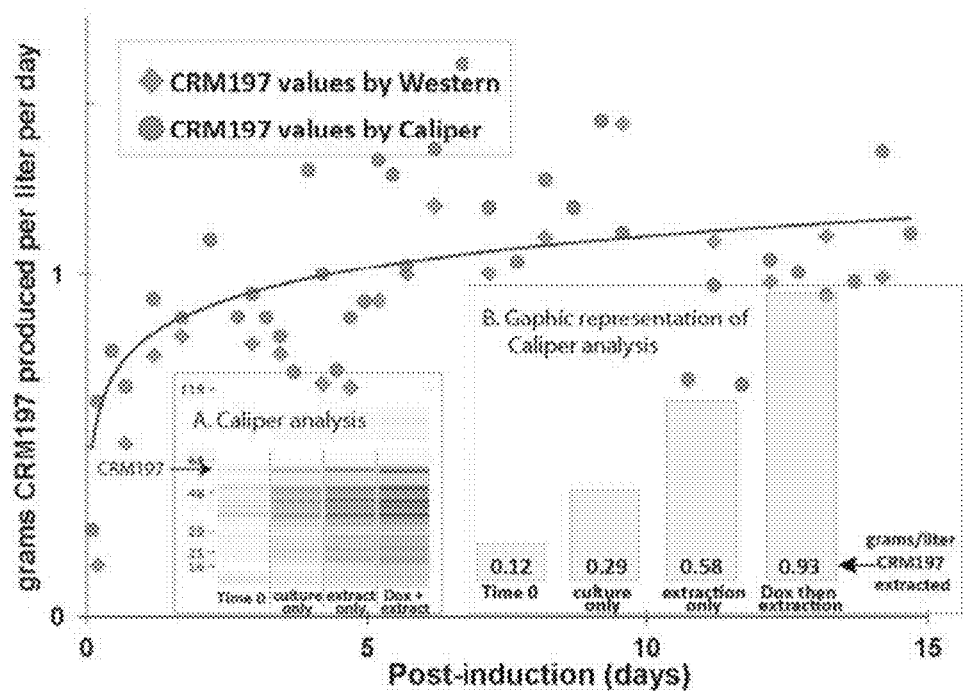
FIG. 16 illustrates extended continuous fermentation (aka continuous flow fermentation or C-flow) of strain SG69meta containing a single expression plasmid comprising sequence encoding CRM197 under the control of an IPTG-inducible promoter and pldA under the control of a doxycycline-inducible promoter. C-flow produced an average of 1 g/L/day as determined by Caliper Labchip and Wes (capillary Western) analysis. Left panel shows Caliper analysis of fermentate from the production tank at 10 days post-IPTG induction of CRM197 expression that was 1) treated with Tris/EDTA and shaken at 25° C. or 2) treated with DOX to induce expression of the pldA gene and then extracted with Tris/EDTA for 16 hours. Graphic representation of Caliper results is shown in the right panel.
Figure 17:
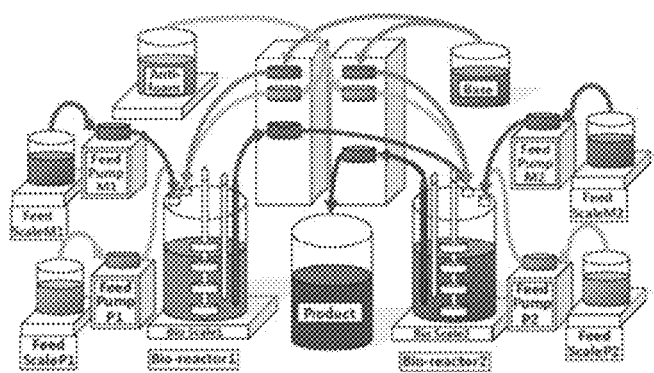
FIG. 17 illustrates an exemplary continuous fermentation apparatus. Bacterial cultures in two chemostat bioreactors are brought at high cell density (~200 $OD_{600}$). Following induction of target gene expression in bioreactor 2, cells containing product are collected at a rate of 1 liter/day (or at a rate appropriate to whatever size fermentation vessel is used). Note that "seed" culture from uninduced bioreactor 1 is transferred to bioreactor 2 to replenish cells removed during product collection. Inducer concentrations are maintained by adding inducer (IPTG is exemplified) to the bioreactor 2 feed.

To determine whether buffer extraction of recombinant proteins in shake-flask culture is scalable to the high bacterial cell densities achieved during continuous fermentation, an extended fermentation using SG69meta (aka MDS69meta aka T69meta) harboring a single expression plasmid comprising sequence encoding CRM197 under the control of an IPTG-inducible promoter and pldA under the control of a doxycycline-inducible promoter used in the shake flask culture experiments described above. An extended fermentation depicting the expression of CRM197 over a 2 week period is shown in FIG. 16. CRM197 expression was on average 1 g/L/day and the fermentation maintained a relatively consistent, high-density $OD_{600}$ of 200. Extraction experiments performed on the high-density continuous fermentation fermentate resulted in 90% recovery of CRM197 (see panel A and B of FIG. 16). In the experiment shown, 100 ml of undiluted fermentate was taken from 1-liter batch collection vessels. Doxycycline was then added to the 100 ml fermentation aliquots and the samples incubated for 4 hours in a shaking chest incubator with agitation at 25° C. Extraction buffer was added (equal to $1/10^{th}$ volume of fermentate) and the samples incubated for an additional 16 hours. Although Tris/EDTA extraction in the absence of DOX induction resulted in the extraction of about half of the CRM197 present in the periplasm (due to uninduced expression of ompLA), DOX induction coupled with Tris/EDTA resulted in the extraction of 90% of CRM197. These results demonstrate that the extraction methods described herein are adaptable to high density continuous fermentation.

Continuous fermentation of reduced genome *E. coli* strains (which can be grown to an extremely high density) carrying expression plasmid(s) encoding a target protein (e.g. a carrier protein) fused to a periplasmic signal sequence and an *E. coli* phospholipase (with the carrier protein and phospholipase regulated by a single promoter or by separate promoters) as herein described enables long-term high yield production of the encoded protein and complete extraction of the target protein into the media with a simple buffer, greatly simplifying downstream processing (e.g. purification) steps.

Importantly, production of CRM197 and other carrier proteins is not feasible in commercial *E. coli* B strains such as BL21 and BLR nor is it feasible in *E. coli* K12 strain MG1655, the parent strain of the reduced genome *E. coli* strains described herein. Using these strains, continuous fermentation is not possible for longer than 7 days and production of CRM197 quickly falls from about 1 g/L/day to about 0 g/L/day. Using reduced genome *E. coli* strains as described herein, continuous fermentation runs of up to 65 days have been achieved with consistent production of PD at ~9 g/L/day and up to 30 days with consistent production of CRM197 at ~4-5 g/L/day, with greatly improved purification from the media possible with co-expression of a lipase. There appears to be no limitation on extending continuous flow to 365 days or more of continuous production.

Optional Downstreaming Processing

Continuous culture (aka continuous flow or "C-Flow") may comprise a downstream culture cleaning process for continuous, automatic clearing to remove intact cells or debris from the fermentation supernatant and may comprise a miniaturized, low-cost chromatography system for easy purification of the desired product from the cleared supernatant by concurrently linking the chromatography processes with the flow rates of the continuous culture.

CRM197 produced using the compositions and methods described herein is highly consistent, up to 98% pure, contains no methylation, acetylation, gluconoylation or phosphorylation, and has extremely low endotoxin levels (<25 EU/mg). Considering the amount of CRM197 per dose in commercial vaccines ranges between 12 and 65 ug, the potential endotoxin contamination would be less than 0.5 EU per dose for a standard vaccine, well below the industry standard of <10 EU/dose for polysaccharide vaccines.

Example 7

Deletion of Toxin-Antitoxin Genes Significantly Improves Production of Carrier Proteins The effect of deleting toxin-antitoxin genes on production of carrier proteins in E. coli was assessed. The following toxin-antitoxin genes were deleted from several MDS E. coli strains to create the corresponding MDS T/A strains: YafQ, dinJ, hha, tomB, gnsA, ymcE, yoeB, yefM, mazF, mazE, mazG, cptA/ygfX, cptB/sdhE, mqsR, mqsA, higB, higA, yhaV, prlF, ldrD, rdlD, istR-2, tisB, chpB, chpS, ratA, ratB, ldrA, rdlA, ldrB, rdlB, ldrC, rdlC, hokB, sokB, sibA, ibsA, sibB, ibsB, ohsC, shoB, sibC, ibsC, sibD, sibE, ibsD, ibsE, dinQ, agrA, agrB, ghoT, ghoS, yfeC, yfeD, fic, yhfG, yhjJ, yhjM, yhjN, yjjJ, ecnA, and ecnB.

Production of CRM197, EPA and PD were assessed in MDS69meta rec A (comprising toxin-antitoxin genes) and in the following derivative strains from which toxin-antitoxin genes had been deleted: MDS69meta T/A recA and MDS69meta T/A LowMut recA.

The periplasmic yields of CRM197, PD and EPA were assessed in each of the host strains carrying an expression plasmid encoding CRM197, EPA or PD fused to a YtfQ secretion signal under the control of an IPTG-inducible or doxycycline-inducible promoter.

For CRM197 with IPTG induction, 3 colonies from each strain were used to inoculate separate flasks, 25 ml Kor/0.2% Glucose/Kan (25 µg/ml) at 37° C. The 25 ml inoculums were used to inoculate subsequent 100 ml cultures to an OD600=0.25 in 500 ml baffled E-flasks. All cultures were grown at 25° C. to the following approximate OD600 (corrected): 2.8 for MDS69meta recA (SG7766 in Table 3 below); 3.0 for MDS69meta T/A LowMut recA (SG8081 in Table 3 below). 20 ml aliquots were then removed, placed in 125 ml baffled E-flasks and induced with 25 µM, 50 µM, 100 µM or 200 µM IPTG and the cultures were shaken overnight at 25° C. After 16-20 hours of incubation at 25° C., 2 ODs of cultures were harvested by cfg (10 min at 7500×g) and periplasm was isolated in triplicate from 2 ODs (15 min at 4000×g) by EpiCentre periplasmic preparation Method. All samples were final concentration 0.02 OD/µl, analyzed on the same Caliper chip on the same run.

As can be seen from Table 3 below, production of CRM197 was significantly increased in strains from which toxin-antitoxin genes are deleted (~38% increase in CRM197):

TABLE 3

| Clone | IPTG | Avg ALL Clones SG7766 or SG8081 g/L | STD DEV ALL Clones | Average % Purity of CRM197 |
|---|---|---|---|---|
| SG7766-A, B, C | 25 µM | 2.17 | 0.62 | 44 |
|  | 50 µM | 2.60 | 0.64 | 46 |
|  | 100 µM | 2.61 | 0.54 | 48 |
|  | 200 µM | 2.53 | 0.23 | 47 |

TABLE 3-continued

| Clone | IPTG | Avg ALL Clones SG7766 or SG8081 g/L | STD DEV ALL Clones | Average % Purity of CRM197 |
|---|---|---|---|---|
| SG8081-D, E. G | 25 µM | 2.61 | 0.33 | 63 |
|  | 50 µM | 2.93 | 0.30 | 66 |
|  | 100 µM | 3.59 | 0.41 | 70 |
|  | 200 µM | 3.16 | 0.39 | 65 |

For EPA and PD with IPTG induction, 3 colonies from each strain were used to inoculate separate flasks, 25 ml Kor/0.2% Glucose/Kan at 37° C. The 25 ml inoculums were used to inoculate subsequent 100 ml cultures to an OD600=0.25 in 500 ml baffled E-flasks. All cultures were grown at 25° C. to saturation, OD600 m (corrected): 2.9 for MDS69meta recA and 3.2 for MDS69meta T/A LowMut recA. 20 ml aliquots were then removed, placed in 125 ml baffled E-flasks and induced with 25 µM, 50 µM, 100 µM or 200 µM IPTG overnight at 25° C. After 16-20 hours of incubation at 25° C., 2 ODs of cultures were harvested by centrifugation (10 min at 7500×g) and periplasmic contents were isolated in triplicate from 2 ODs (15 min at 4000×g) by EpiCentre periplasmic preparation Method. All samples were final concentration 0.02 OD/µl, analyzed on the same Caliper chip on the same run.

As can be seen from Table 4 below, production of PD was significantly increased in strains from which toxin-antitoxin genes are deleted (~25% increase in PD):

TABLE 4

| Clone | IPTG | Avg g/L | STD DEV | Average % Purity | |
|---|---|---|---|---|---|
| SG8415 | 25 µM | 2.79 | 0.44 | 57 | rEPA |
| T69 Meta recA | 50 µM | 4.75 | 0.38 | 64 | |
| ytfQ-rEPA | 100 µM | 5.13 | 0.45 | 66 | |
|  | 200 µM | 6.27 | 0.96 | 67 | |
| SG8975-76 | 25 µM | 2.79 | 0.96 | 62 | |
| T69 Meta T/AT | 50 µM | 4.43 | 0.88 | 66 | |
| LowMut recA | 100 µM | 4.69 | 0.30 | 67 | |
| ytfQ-rEPA | 200 µM | 5.96 | 0.47 | 67 | |
| SG8506 | 25 µM | 4.10 | 0.13 | 76 | Protein D |
| T69 Meta recA | 50 µM | 5.97 | 0.39 | 83 | |
| ytfQ-Protein D | 100 µM | 6.77 | 0.39 | 86 | |
|  | 200 µM | 7.59 | 0.55 | 86 | |
| SG8977-78 | 25 µM | 5.7 | 0.29 | 81 | |
| T69 Meta T/AT | 50 µM | 8.45 | 0.34 | 81 | |
| LowMut recA | 100 µM | 8.71 | 0.78 | 87 | |
| ytfQ-Protein D | 200 µM | 9.49 | 0.40 | 88 | |

SG8415 and SG8506 are each a single clone

Next, periplasmic yield of CRM197 was assessed in three strains carrying an expression plasmid encoding CRM197 fused to ytfQ signal sequence under the control of dual tetO operators/tet repressor (two copies of the operator but only one copy of the tet repressor): (i) MDS69meta RecA (aka T69 Meta recA aka SG69 Meta recA) (ii) MDS69meta T/A recA (aka T69 Meta Tox/Atox recA aka SG69 Meta Tox/Atox recA) and (iii) MDS69meta T/A LowMut recA (aka T69 Meta Tox/Atox LowMut recA aka SG69 Meta Tox/Atox LowMut recA).

Three colonies from each strain were used to inoculate separate flasks, 25 ml Kor/0.2% Glucose/Kan (25 µg/ml) at 37° C. The 25 ml inoculums were used to inoculate subsequent 100 ml cultures to an OD600=0.25 in 500 ml baffled E-flasks. All cultures were grown at 25° C. to saturation. 20 ml aliquots were then removed, placed in 125 ml baffled E-flasks and induced with 50 or 100 nM DOX overnight at 25° C. After 16-20 hours of incubation at 25° C., 2 ODs of cultures were harvested by centrifugation (10 min at 7500× g) and periplasmic, proteins were isolated in triplicate from 2 ODs (15 min at 4000×g) by EpiCentre periplasmic preparation Method. All samples were final concentration 0.02 OD/μl, analyzed on the same Caliper chip on the same run.

Deletion of the toxin/antitoxin genes significantly enhanced the yield of CRM197 in the periplasm (from 3.9 g/L to 5.1 g/L, Table 5 below; see also FIG. 18).

TABLE 5

| Periplasm Prep | Clone | DOX | Extrapolated Avg g/L at 250 OD | STD DEV | Average % Purity |
|---|---|---|---|---|---|
| CRM197 | SG9461-62 T69 Meta recA pSG9353 (ytfQ-CRM197) | 50 + 100 nm | 3.9 | 0.1 | 64% |
|  | SG9457 T69 Meta Tox/ ATox recA pSG9353 (ytfQ-CRM197) | 50 + 100 nm | 5.1 | 0.5 | 69% |
|  | SG9369 T69 Meta Tox/ ATox LowMut recA pSG9353 (ytfQ-CRM197) | 50 + 100 nm | 5.1 | 0.2 | 68% |

These results demonstrate the advantage of *E. coli* strains having toxin-antitoxin genes deleted therefrom. These advantages do not seem to be limited to any particular *E. coli* strain.

Example 8

OmpLA Co-Expression Facilitates Complete Extraction of Recombinant Antibodies

Next, the extraction of relevant recombinant proteins was expanded to include a single chain antibody (scFab YMF10) and a single-chain variable fragment (scFv 75127, gift of Fritz Schaumburg, Lytic Solutions, Madison, WI). Both targets represent highly relevant recombinant therapeutic proteins. Briefly, MDS69meta RecA (aka T69 Meta RecA aka SG69meta RecA) carrying an expression plasmid encoding either antibody fused to an OmpA periplasmic signal sequence under IPTG control and encoding OmpLA under control of a dual-tetO DOX-inducible promoter were induced (very late induction) with 100 μM IPTG and 4 hours later with 0, 50 or 100 nM DOX to induce pldA. Following overnight induction, 1335 ml of culture was placed in a 2 ml tube containing concentrated Tris and EDTA (final concentration=1.5 ml, 150 mM Tris pH 7.75, 5 mM EDTA) and incubated at 25° C. overnight with shaking. For periplasm, an Epicentre Peri-Prep was performed on a separate aliquot of culture, final concentration=0.02 OD/μl. All samples were analyzed on a Caliper chip.

Figure 19:
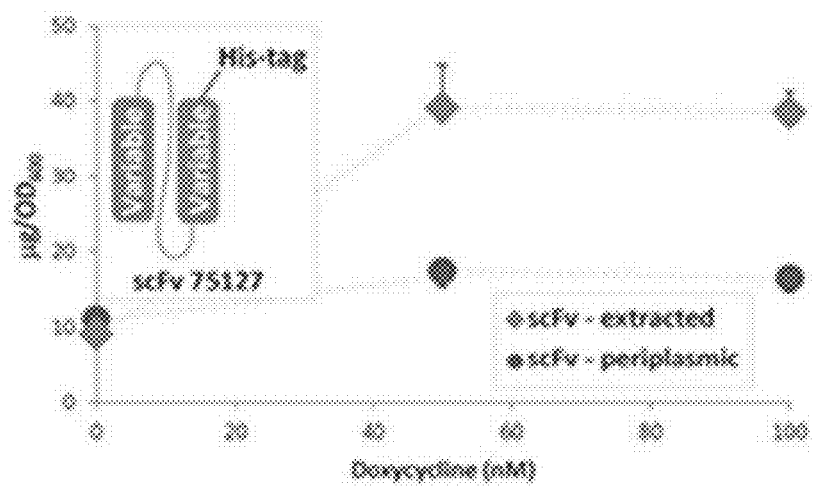
FIGS. 19A-B illustrate extraction of a single chain variable fragment, scFv 75127 (provided by Fritz Schaumburg, Lytic Solutions, Madison WI) (FIG. 19A), and a single chain antibody, scFab YMF10 (FIG. 19B) from shake-flask culture following OmpLA expression.
Figure 19:
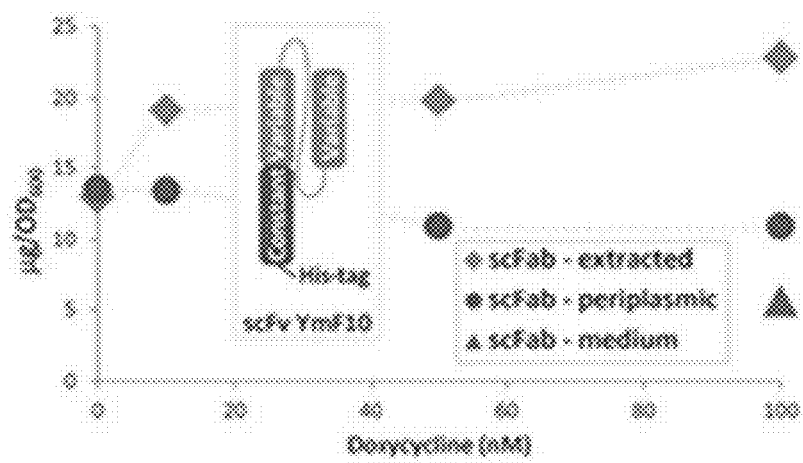
Figure 20A:
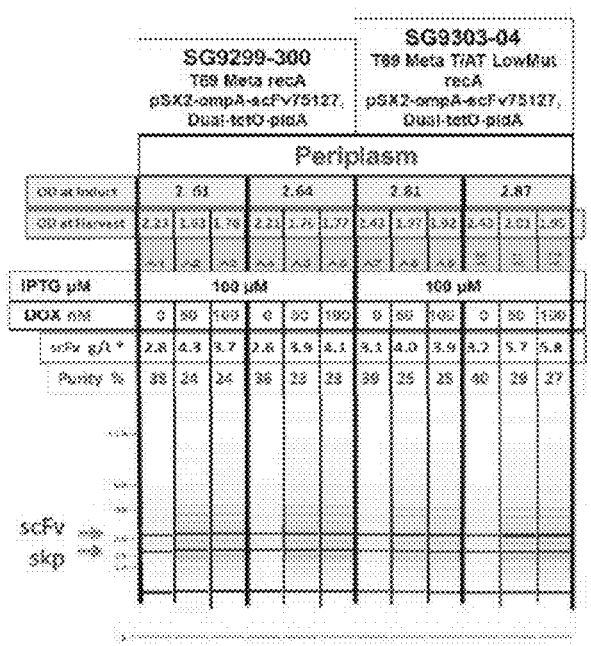
Figure 20B:
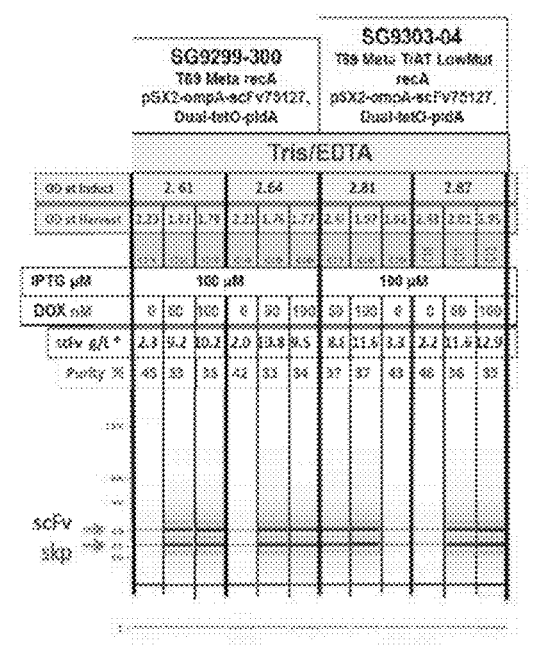

High levels of expression followed by periplasmic delivery of the scFv (scFv was co-expressed with the chaperon protein skp, which provided proper folding in the periplasm) was observed. High amounts of scFv 75127 were present in culture medium after extraction (FIG. 19A), levels that were much higher than those observed in the periplasm. See also FIGS. 20A and 20B illustrating periplasmic yield and extracted yield of scFv 75127. These results confirm that the expression and extraction methods that produce high amounts of carrier protein function well for single chain antibodies as well.

Figure 21A:
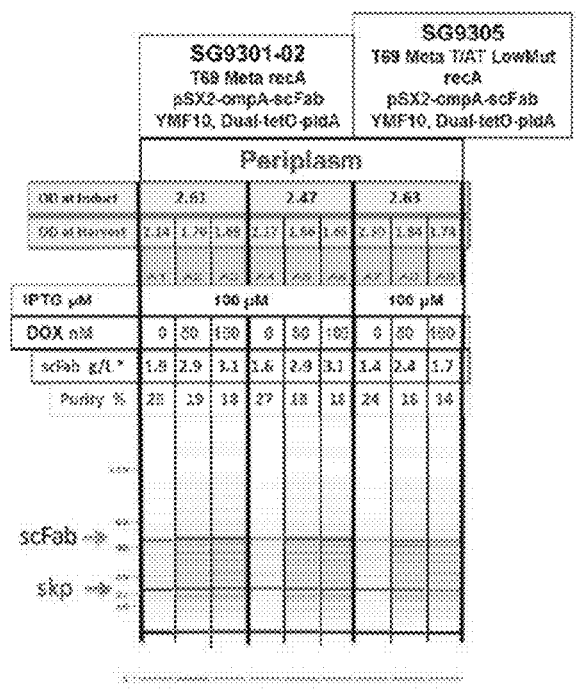
FIGS. 21A-B illustrate periplasmic (FIG. 21A) and extracted yield (FIG. 21B) of scFab YMF10 in MDS69meta recA (aka T69 Meta recA) and MDS69meta T/AT LowMut RecA (aka T69 Meta T/AT LowMut recA) strain carrying an expression plasmid encoding the scFab fused to an OmpA secretion signal under the control of an IPTG-inducible promoter and pldA under the control of a DOX-inducible promoter. scFab expression was induced and four hours later expression of pldA was induced and induction continued overnight at which time cells were contacted with Tris/EDTA extraction buffer (as described above) overnight at 25° C.
Figure 21B:
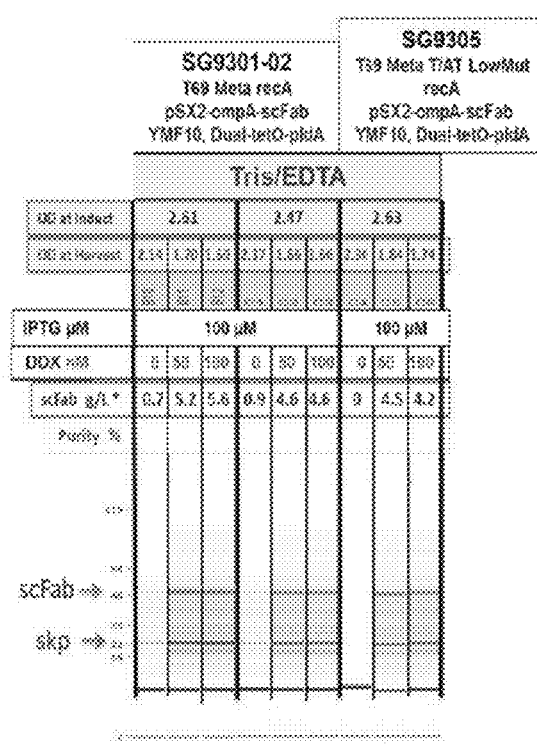

The expression and extraction of the single chain antibody scFab YMF10 was also examined. scFab YMF10 is highly susceptible to degradation in conventional *E. coli* expression strains and was found to undergo slow degradation in MDS69meta (aka SG69meta aka T69meta). To eliminate the degradation problem, an SG69 expression strain that has additional proteases removed compared to SG69meta was employed. Stable expression of scFab YMF10 (and the chaperone, skp) was accomplished in this protease reduced strain (FIG. 19B). See also FIGS. 21A and 21B illustrating periplasmic yield and extracted yield of scFab YMF10. Like scFv, higher amounts of scFab YMF10 were evident in extracted samples than in Epicentre periplasmic isolation samples. Small amounts of scFab were present in the medium prior to extraction (green triangle in FIG. 19B), which may explain this discrepancy. These results emphasize the versatility of both the novel extraction method and the reduced genome *E. coli* bacteria described herein.

We claim:

1. A non-naturally occurring *E. coli* bacterium having a genome between 4.41 Mb and 2.78 Mb and lacking at least the following toxin-antitoxin genes: yafQ, dinJ, hha, tomB, gnsA, ymcE, yoeB, yefM, mazF, mazE, mazG, cptA/ygfX, cptB/sdhE, mqsR, mqsA, higB, higA, yhaV, prlF, ldrD, rdlD, istR-2, tisB, chpB, chpS, ratA, ratB, ldrA, rdlA, ldrB, rdlB, ldrC, rdlC, hokB, sokB, sibA, ibsA, sibB, ibsB, ohsC, shoB, sibC, ibsC, sibD, sibE, ibsD, ibsE, dinQ, agrA, agrB, ghoT, ghoS, yfeC, yfeD, fic, yhfG, yhjJ, yhjM, yhjN, yjjJ, ecnA, and ecnB.

2. The bacterium according to claim 1, comprising a full or partial deletion of the rnc gene.

3. The bacterium according to claim 1, wherein the bacterium additionally lacks all IS1, IS2, IS3, IS5, IS150 and IS186 insertion sequences.

4. The bacterium according to claim 1, wherein the bacterium additionally comprises a deletion of the dinB gene.

5. The bacterium according to claim 1, wherein the bacterium additionally comprises a deletion of the recA gene.

6. The bacterium according to claim 1, wherein the parent strain of said bacterium is a K-12 or B strain.

7. The bacterium according to claim 6, wherein the parent strain of said bacterium is a K-12 strain.

8. The bacterium according to claim 7, wherein the bacterium additionally comprises one or more of the following modifications: (i) deletion of the rph gene to enhance orotate phosphoribosyltransferase activity (ii) correction of the native-2 frameshift mutation in the ilvG gene in order to restore the active acetohydroxy acid synthase II production and (iii) deletion of all or part of the iclR and arpA genes.

9. The bacterium according to claim 7, wherein the parent strain of said bacterium is K-12 strain MG1655.

10. The bacterium according to claim 9, wherein the bacterium lacks at least the following genes of the *E. coli* K-12 strain MG1655: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945 or lacks the corresponding genes on a different K-12 or B strain.

11. The bacterium according to claim 9, wherein the bacterium lacks at least the following genes of the *E. coli* K-12 strain MG1655: b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153, b2945, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, and b0502 or lacks the corresponding genes on a different K-12 or B strain.

12. The bacterium according to claim 1, comprising a nucleic acid comprising a nucleotide sequence encoding a recombinant polypeptide, said nucleotide sequence operably linked to an expression control sequence.

13. The bacterium according to claim 8, wherein the bacterium additionally comprises all of the following modifications: (i) deletion of the rph gene to enhance orotate phosphoribosyltransferase activity (ii) correction of the native-2 frameshift mutation in the ilvG gene in order to restore the active acetohydroxy acid synthase II production and (iii) deletion of all or part of the iclR and arpA genes.

* * * * *

SEQUENCE LISTING

```
Sequence total quantity: 9
SEQ ID NO: 1           moltype = AA  length = 358
FEATURE                Location/Qualifiers
source                 1..358
                       mol_type = protein
                       organism = Escherichia coli
SEQUENCE: 1
MKLTLKNLSM AIMMSTIVMG SSAMAADSNE KIVIAHRGAS GYLPEHTLPA KAMAYAQGAD    60
YLEQDLVMTK DDNLVVLHDH YLDRVTDVAD RFPDRARKDG RYYAIDFTLD EIKSLKFTEG   120
FDIENGKKVQ TYPGRFPMGK SDFRVHTFEE EIEFVQGLNH STGKNIGIYP EIKAPWFHHQ   180
EGKDIAAKTL EVLKKYGYTG KDDKVYLQCF DADELKRIKN ELEPKMGMEL NLVQLIAYTD   240
WNETQQKQPD GSWVNYNYDW MFKPGAMKQV AEYADGIGPD YHMLIEETSQ PGNIKLTGMV   300
QDAQQNKLVV HPYTVRSDKL PEYTPDVNQL YDALYNKAGV NGLFTDFPDK AVKFLNKE    358

SEQ ID NO: 2           moltype = AA  length = 319
FEATURE                Location/Qualifiers
source                 1..319
                       mol_type = protein
                       organism = Escherichia coli
SEQUENCE: 2
MKPENKLPVL DLISAEMKTV VNTLQPDLPP WPATGTIAEQ RQYYTLERRF WNAGAPEMAT    60
```

```
RAYMVPTKYG QVETRLFCPQ PDSPATLFYL HGGGFILGNL DTHDRIMRLL ASYSQCTVIG    120
IDYTLSPEAR FPQAIEEIVA ACCYFHQQAE DYQINMSRIG FAGDSAGAML ALASALWLRD    180
KQIDCGKVAG VLLWYGLYGL RDSVTRRLLG GVWDGLTQQD LQMYEEAYLS NDADRESPYY    240
CLFNNDLTRE VPPCFIAGAE FDPLLDDSRL LYQTLAAHQQ PCEFKLYPGT LHAFLHYSRM    300
MKTADEALRD GAQFFTAQL                                                319

SEQ ID NO: 3               moltype = AA   length = 340
FEATURE                    Location/Qualifiers
source                     1..340
                           mol_type = protein
                           organism = Escherichia coli
SEQUENCE: 3
MFQQQKDWET RENAFAAFTM GPLTDFWRQR DEAEFTGVDD IPVRFVRFRA QHHDRVVVIC     60
PGRIESYVKY AELAYDLFHL GFDVLIIDHR GQGRSGRLLA DPHLGHVNRF NDYVDDLAAF    120
WQQEVQPGPW RKRYILAHSM GGAISTLFLQ RHPGVCDAIA LTAPMFGIVI RMPSFMARQI    180
LNWAEAHPRF RDGYAIGTGR WRALPFAINV LTHSRQRYRR NLRFYADDPT IRVGGPTYHW    240
VRESILAGEQ VLAGAGDDAT PTLLLQAEEE RVVDNRMHDR FCELRTAAGH PVEGGRPLVI    300
KGAYHEILFE KDAMRSVALH AIVDFFNRHN SPSGNRSTEV                          340

SEQ ID NO: 4               moltype = AA   length = 289
FEATURE                    Location/Qualifiers
source                     1..289
                           mol_type = protein
                           organism = Escherichia coli
SEQUENCE: 4
MRTLQGWLLP VFMLPMAVYA QEATVKEVHD APAVRGSIIA NMLQEHDNPF TLYPYDTNYL     60
IYTQTSDLNK EAIASYDWAE NARKDEVKFQ LSLAFPLWRG ILGPNSVLGA SYTQKSWWQL    120
SNSEESSPFR ETNYEPQLFL GFATDYRFAG WTLRDVEMGY NHDSNGRSDP TSRSWNRLYT    180
RLMAENGNWL VEVKPWYVVG NTDDNPDITK YMGYYQLKIG YHLGDAVLSA KGQYNWNTGY    240
GGAELGLSYP ITKHVRLYTQ VYSGYGESLI DYNFNQTRVG VGVMLNDLF                289

SEQ ID NO: 5               moltype = AA   length = 208
FEATURE                    Location/Qualifiers
source                     1..208
                           mol_type = protein
                           organism = Escherichia coli
SEQUENCE: 5
MMNFNNVFRW HLPFLFLVLL TFRAAAADTL LILGDSLSAG YRMSASAAWP ALLNDKWQSK     60
TSVVNASISG DTSQQGLARL PALLKQHQPR WVLVELGGND GLRGFQPQQT EQTLRQILQD    120
VKAANAEPLL MQIRLPANYG RRYNEAFSAI YPKLAKEFDV PLLPFFMEEV YLKPQWMQDD    180
GIHPNRDAQP FIADWMAKQL QPLVNHDS                                      208

SEQ ID NO: 6               moltype = AA   length = 345
FEATURE                    Location/Qualifiers
source                     1..345
                           mol_type = protein
                           organism = Haemophilus influenzae
SEQUENCE: 6
SSHSSNMANT QMKSDKIIIA HRGASGYLPE HTLESKALAF AQQADYLEQD LAMTKDGRLV     60
VIHDHFLDGL TDVAKKFPHR HRKDGRYYVI DFTLKEIQSL EMTENFETKD GKQAQVYPNR    120
FPLWKSHFRI HTFEDEIEFI QGLEKSTGKK VGIYPEIKAP WPHHQNGKDI AAETLKVLKK    180
YGYDKKTDMV YLQTFDFNEL KRIKTELLPQ MGMDLKLVQL IAYTDWKETQ EKDPKGYWVN    240
YNYDWMFKPG AMAEVVKYAD GVGPGWYMLV NKEESKPDNI VYTPLVKELA QYNVEVHPYT    300
VRKDALPEFF TDVNQMYDAL LNKSGATGVF TDFPDTGVEF LKGIK                    345

SEQ ID NO: 7               moltype = DNA   length = 95
FEATURE                    Location/Qualifiers
misc_feature               1..95
                           note = CRM197 Expression Plasmid Sequence
source                     1..95
                           mol_type = other DNA
                           organism = synthetic construct
SEQUENCE: 7
aaactgagcc tgttctttga gatcaaaagc taatcggctg ctaacaaagc ccgaaaggaa     60
gctgagttgg ctgctgccac cgctgctggt tcgct                               95

SEQ ID NO: 8               moltype = DNA   length = 109
FEATURE                    Location/Qualifiers
misc_feature               1..109
                           note = CRM197 Expression Plasmid Derivative 1
source                     1..109
                           mol_type = other DNA
                           organism = synthetic construct
SEQUENCE: 8
aaactgagcc tgttctttga gatcaaaagc taatcgatat cgcaagcttt aagaggacaa     60
cattatgcgg actctgcagg gctggttgtt ccggtgtttg atgttgcct                109

SEQ ID NO: 9               moltype = DNA   length = 108
FEATURE                    Location/Qualifiers
```

```
misc_feature      1..108
                  note = CRM197 Expression Plasmid Derivative 2
source            1..108
                  mol_type = other DNA
                  organism = synthetic construct
SEQUENCE: 9
aaactgagcc tgttctttga gatcaaaagc taatcgatat cgcaatcttt aaaggacaac    60
attatgcgga ctctgcaggg ctggttgttg ccggtgttta tgttgcct               108
```